US006267956B1

(12) United States Patent
Gomes et al.

(10) Patent No.: US 6,267,956 B1
(45) Date of Patent: Jul. 31, 2001

(54) PROTEIN ACTIVATOR AND APOPTOSIS

(75) Inventors: Bruce Charles Gomes, Elkton, MD (US); Garrett M. Kasof, Bear; Judith Caroline Prosser, Hockessin, both of DE (US)

(73) Assignee: Zeneca Ltd. (GB)

( * ) Notice: Subject to any disclaimer, the term of this patent is extended or adjusted under 35 U.S.C. 154(b) by 0 days.

(21) Appl. No.: 09/531,914

(22) Filed: Mar. 21, 2000

Related U.S. Application Data

(62) Division of application No. 09/329,418, filed on Jun. 10, 1999, now Pat. No. 6,096,539.

(51) Int. Cl.$^7$ .............................. A61K 38/43; C12N 9/00; C07K 14/00
(52) U.S. Cl. .................... 424/94.1; 435/183; 530/350
(58) Field of Search ........................ 435/183; 424/94.1; 8/563; 530/402, 350

(56) References Cited

PUBLICATIONS

M. Kelliher et al., "The Death Domain Kinase RIP Mediates the TNF–Induced NF–kB Signal", *Immunity*, vol. 8, pp. 297–303, Mar., 1998.

B. Stanger et al. "RIP: A Novel Protein Containing a Death Domain That Interacts with Fas/APO–1 (CD95) in Yeast and Causes Cell Death", *Cell*, vol. 81, pp. 513–523, May 19, 1995.

Y. Jiang et al., "Prevention of Constitutive TNF Receptor 1 Signaling by Silencer of Death Domains", *Science*, vol. 283, pp. 543–546, Jan. 22, 1999.

M. Cardone et al., "Regulation of Cell Death Protease Caspase–9 by Phosphorylation", *Science*, vol. 282, pp. 1318–1321, Nov. 13, 1998.

L. Miller et al., "Apoptosis", *Science*, vol. 281, p. 1301, Aug. 28, 1998.

M. Barinaga, "Stroke–Damaged Neurons May Commit cellular Suicide", *Science*, vol. 281, pp. 1302–1304, Aug. 28, 1998.

A. Ashkenazi et al., "Death Receptors: Signaling and Modulation", *Science*, vol. 281, pp. 1305–1308, Aug. 28, 1998.

D. Green et al., "Mitochondria and Apoptosis", *Science*, vol. 281, pp. 1309–1316, Aug. 28, 1998.

N. A. Thornberry et al., "Caspases: Enemies Within", *Science*, vol. 281, pp. 1312–1316, Aug. 28, 1998.

G. Evan et al., "A Matter of Life and Cell Death", *Science*, vol. 281, pp. 1321–1326, Aug. 28, 1998.

J. M. Adams et al., "The Bcl–2 Protein Family: Arbiters of Cell Survival", Science, vol. 281, pp. 1322–1326, Aug. 28, 1998.

M. Hengartner et al., "Death by Crowd Control", *Science*, vol. 281, pp. 1298–1299, Aug. 28, 1998.

X. Yang et al., "Essential Role of CED–4 Oligomerization in CED–3 Activation and Apoptosis", *Science*, vol. 281, pp. 1355–1357, Aug. 28, 1998.

X. Sun et al., "RIP3, a Novel Apoptosis–inducing Kinase", *The Journal of Biological Chemistry*, vol. 274, No. 24, Issue of Jun. 11, pp. 16871–16875, 1999.

*Primary Examiner*—Robert A. Schwartzman
*Assistant Examiner*—Janet Epps
(74) *Attorney, Agent, or Firm*—Kenneth F. Mitchell

(57) ABSTRACT

An isolated and purified human protein activator of apoptosis is described. A cDNA sequence which encodes the native kinase of death is disclosed as well as the structural coding region and the amino acid residue sequence. Methods are provided which employ the sequences to identify compounds that modulate the biological and/or pharmacological activity of the activator and hence regulate apoptosis. Biologically-effective antisense molecules, as well as dominant negative mutant versions of the apoptosis activator are described which are suitable for therapeutic use. The invention is also drawn toward the study, prevention, diagnosis, and treatment of pathophysiological disorders related to apoptosis.

5 Claims, 1 Drawing Sheet

SEQUENCE LISTING

<160> NUMBER OF SEQ ID NOS: 39

<210> SEQ ID NO 1
<211> LENGTH: 1873
<212> TYPE: DNA
<213> ORGANISM: Homo Sapiens

<400> SEQUENCE: 1

```
gaaaaagggt aacaacccgg aaagtagact caccgtcttg gtctagagac tgacccctgc      60
acagacagac cccttcccct ctctgcgaaa ggaccaagcc ccagaagtca ctccatctcc     120
tacggctcgc aatttccaga ggcccctgg caccttccag cctgatgtcg tgcgtcaagt     180
tatggcccag cggtgccccc gccccttgg tgtccatcga ggaactggag aaccaggagc     240
tcgtcggcaa aggcgggttc ggcacagtgt tccgggcgca acataggaag tggggctacg     300
atgtggcggt caagatcgta aactcgaagg cgatatccag ggaggtcaag gccatggcaa     360
gtctggataa cgaattcgtg ctgcgcctag aagggttat cgagaaggtc ggcggctcga     420
gccaagatcc caagccggct ctggtgacta aattcatgga gaacggctcc ttgtcggggc     480
tgctgcagtc ccagtgccct cggccctggc cgctcctttg ccgcctgctg aaagaagtgg     540
tgcttgggat gttttacctg cacgaccaga acccggtgct cctgcaccgg gacctcaagc     600
catccaacgt cctgctggac ccagagctgc acgtcaagct ggcagatttt ggcctgtcca     660
catttcaggg aggctcacag tcaggacag ggtccgggga gccaggggc accctgggct     720 acttggcccc agaactgttt gttaacgtaa accggaaggc ctccacagcc agtgacgtct     780
acagcttcgg gatcctaatg tgggcagtgc ttgctggaag agaagttgag ttgccaaccg     840
aaccatcact cgtgtacgaa gcagtgtgca acaggcagaa ccggccttca ttggctgagc     900
tgccccaagc cgggcctgag actcccggct tagaaggact gaaggagcta atgcagctct     960
gctggagcag tgagcccaag gacagaccct ccttccagga atgcctacca aaaactgatg    1020
aagtcttcca gatggtggag aacaatatga atgctgctgt ctccacggta aaggatttcc    1080
tgtctcagct caggagcagc aataggagat tttctatccc agagtcaggc caaggaggga    1140
cagaaatgga tggctttagg agaaccatag aaaaccagca ctctcgtaat gatgtcatgg    1200
tttctgagtg gctaaacaaa ctgaatctag aggagcctcc cagctctgtt cctaaaaaat    1260
gcccgagcct taccaagagg agcagggcac aagaggagca ggttccacaa gcctggacag    1320
caggcacatc ttcagattcg atggcccaac ctccccagac tccagagacc tcaactttca    1380
gaaaccagat gcccagccct acctcaactg gaacaccaag tcctggaccc cgagggaatc    1440 aggggctga gagacaaggc atgaactggt cctgcaggac cccggagcca aatccagtaa    1500
cagggcgacc gctcgttaac atatacaact gctctggggt gcaagttgga gacaacaact    1560
acttgactat gcaacagaca actgccttgc ccacatgggg cttggcacct tcgggcaagg    1620
```

| ggagggcett gcagcacccc ccaccagtag gttcgcaaga aggccctaaa gatcctgaag | 1680 |
| cctggagcag gccacagggt tggtataatc atagcgggaa ataaagcacc ttccaagctt | 1740 |
| gcctccaaga gttacgagtt aaggaagagt gccaccccett gaggccctg acttccttct | 1800 |
| agggcagtct ggcctgccca caaactgact ttgtgacctg tcccccagga gtcaataaac | 1860 |
| atgatggaat gct | 1873 |

<210> SEQ ID NO 2
<211> LENGTH: 1557
<212> TYPE: DNA
<213> ORGANISM: Homo Sapiens

<400> SEQUENCE: 2

| atgtcgtgcg tcaagttatg gcccagcggt gcccccgccc ccttggtgtc catcgaggaa | 60 |
| ctggagaacc aggagctcgt cggcaaaggc gggttcggca cagtgttccg ggcgcaacat | 120 |
| aggaagtggg gctacgatgt ggcggtcaag atcgtaaact cgaaggcgat atccagggag | 180 |
| gtcaaggcca tggcaagtct ggataacgaa ttcgtgctgc gcctagaagg ggttatcgag | 240 |
| aaggtgaact gggaccaaga tcccaagccg gctctggtga ctaaattcat ggagaacggc | 300 |
| tccttgtcgg ggctgctgca gtcccagtgc cctyggccct ggccgctcct ttgccgcctg | 360 |
| ctgaaagaag tggtgcttgg gatgttttac ctgcacgacc agaacccggt gctcctgcac | 420 |
| cgggacctca agccatccaa cgtcctgctg acccagagc tgcacgtcaa gctggcagat | 480 |
| tttggcctgt ccacatttca ggaggctca cagtcaggga cagggtccgg ggagccaggg | 540 |
| ggcacectgg gctacttggc cccagaactg tttgttaacg taaaccggaa ggcctccaca | 600 |
| gccagtgacg tctacagctt cgggatccta atgtgggcag tgcttgctgg aagagaagtt | 660 |
| gagttgccaa ccgaaccatc actcgtgtac gaagcagtgt gcaacaggca gaaccggcct | 720 |
| tcattggctg agctgcccca gccgggcct gagactcccg gcttagaagg actgaaggag | 780 |
| ctaatgcagc tctgctggag cagtgagccc aaggacagac cctccttcca ggaatgccta | 840 |
| ccaaaaactg atgaagtctt ccagatggtg gagaacaata tgaatgctgc tgtctccacg | 900 |
| gtaaaggatt tcctgtctca gctcaggagc agcaatagga gattttctat cccagagtca | 960 |
| ggccaaggag ggacagaaat ggatggcttt aggagaacca tagaaaacca gcactctcgt | 1020 |
| aatgatgtca tggtttctga gtggctaaac aaactgaatc tagaggagcc tcccagctct | 1080 |
| gttcctaaaa aatgcccgag ccttaccaag aggagcaggg cacaagagga gcaggttcca | 1140 |
| caagcctgga cagcaggcac atcttcagat tcgatggccc aacctccccca gactccagag | 1200 |
| acctcaactt tcagaaacca gatgcccagc cctacctcaa ctggaacacc aagtcctgga | 1260 |
| ccccgaggga atcaggggc tgagagacaa ggcatgaact ggtcctgcag gaccccggag | 1320 |
| ccaaatccag taacagggcg accgctcgtt aacatataca actgctctgg ggtgcaagtt | 1380 |
| ggagacaaca actacttgac tatgcaacag caactgcct tgcccacatg gggcttggca | 1440 |
| ccttcgggca aggggagggg cttgcagcac ccccaccag taggttcgca agaaggccct | 1500 |
| aaagatcctg aagcctggag caggccacag ggttggtata atcatagcgg gaaataa | 1557 |

<210> SEQ ID NO 3
<211> LENGTH: 518
<212> TYPE: PRT
<213> ORGANISM: Homo Sapiens

<400> SEQUENCE: 3

-continued

```
Met Ser Cys Val Lys Leu Trp Pro Ser Gly Ala Pro Ala Pro Leu Val
1               5                   10                  15

Ser Ile Glu Glu Leu Glu Asn Gln Glu Leu Val Gly Lys Gly Gly Phe
            20                  25                  30

Gly Thr Val Phe Arg Ala Gln His Arg Lys Trp Gly Tyr Asp Val Ala
        35                  40                  45

Val Lys Ile Val Asn Ser Lys Ala Ile Ser Arg Glu Val Lys Ala Met
50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
                100                 105                 110

Pro Trp Pro Leu Leu Cys Arg Leu Leu Lys Glu Val Val Leu Gly Met
            115                 120                 125

Phe Tyr Leu His Asp Gln Asn Pro Val Leu Leu His Arg Asp Leu Lys
        130                 135                 140

Pro Ser Asn Val Leu Leu Asp Pro Glu Leu His Val Lys Leu Ala Asp
145                 150                 155                 160

Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
            195                 200                 205

Ile Leu Met Trp Ala Val Leu Ala Gly Arg Glu Val Glu Leu Pro Thr
        210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
                245                 250                 255

Gly Leu Lys Glu Leu Met Gln Leu Cys Trp Ser Ser Glu Pro Lys Asp
            260                 265                 270

Arg Pro Ser Phe Gln Glu Cys Leu Pro Lys Thr Asp Glu Val Phe Gln
        275                 280                 285

Met Val Glu Asn Asn Met Asn Ala Ala Val Ser Thr Val Lys Asp Phe
290                 295                 300

Leu Ser Gln Leu Arg Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
                325                 330                 335

Gln His Ser Arg Asn Asp Val Met Val Ser Glu Trp Leu Asn Lys Leu
            340                 345                 350

Asn Leu Glu Glu Pro Pro Ser Ser Val Pro Lys Lys Cys Pro Ser Leu
        355                 360                 365

Thr Lys Arg Ser Arg Ala Gln Glu Glu Gln Val Pro Gln Ala Trp Thr
    370                 375                 380

Ala Gly Thr Ser Ser Asp Ser Met Ala Gln Pro Gln Thr Pro Glu
385                 390                 395                 400

Thr Ser Thr Phe Arg Asn Gln Met Pro Ser Pro Thr Ser Thr Gly Thr
                405                 410                 415

Pro Ser Pro Gly Pro Arg Gly Asn Gln Gly Ala Glu Arg Gln Gly Met
```

```
                        420             425             430
Asn Trp Ser Cys Arg Thr Pro Glu Pro Asn Pro Val Thr Gly Arg Pro
        435                 440                 445

Leu Val Asn Ile Tyr Asn Cys Ser Gly Val Gln Val Gly Asp Asn Asn
    450                 455                 460

Tyr Leu Thr Met Gln Gln Thr Thr Ala Leu Pro Thr Trp Gly Leu Ala
465                 470                 475                 480

Pro Ser Gly Lys Gly Arg Gly Leu Gln His Pro Pro Val Gly Ser
                485                 490                 495

Gln Glu Gly Pro Lys Asp Pro Glu Ala Trp Ser Arg Pro Gln Gly Trp
                500                 505                 510

Tyr Asn His Ser Gly Lys
            515

<210> SEQ ID NO 4
<211> LENGTH: 518
<212> TYPE: PRT
<213> ORGANISM: Artificial Sequence
<220> FEATURE:
<223> OTHER INFORMATION: Dominant Negative Mutant Embodiment

<400> SEQUENCE: 4

Met Ser Cys Val Lys Leu Trp Pro Ser Gly Ala Pro Ala Pro Leu Val
1               5                   10                  15

Ser Ile Glu Glu Leu Glu Asn Gln Glu Leu Val Gly Lys Gly Gly Phe
            20                  25                  30

Gly Thr Val Phe Arg Ala Gln His Arg Lys Trp Gly Tyr Asp Val Ala
        35                  40                  45

Val Lys Ile Val Asn Ser Lys Ala Ile Ser Arg Glu Val Lys Ala Met
    50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
            100                 105                 110

Pro Trp Pro Leu Leu Cys Arg Leu Leu Lys Glu Val Val Leu Gly Met
        115                 120                 125

Phe Tyr Leu His Asp Gln Asn Pro Val Leu Leu His Arg Ala Leu Lys
130                 135                 140

Pro Ser Asn Val Leu Leu Asp Pro Glu Leu His Val Lys Leu Ala Asp
145                 150                 155                 160

Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
        195                 200                 205

Ile Leu Met Trp Ala Val Leu Ala Gly Arg Glu Val Glu Leu Pro Thr
    210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
                245                 250                 255

Gly Leu Lys Glu Leu Met Gln Leu Cys Trp Ser Ser Glu Pro Lys Asp
```

-continued

```
                260                 265                 270
Arg Pro Ser Phe Gln Glu Cys Leu Pro Lys Thr Asp Glu Val Phe Gln
                275                 280                 285
Met Val Glu Asn Asn Met Asn Ala Ala Val Ser Thr Val Lys Asp Phe
            290                 295                 300
Leu Ser Gln Leu Arg Ser Ser Asn Arg Arg Phe Ser Ile Pro Glu Ser
305                 310                 315                 320
Gly Gln Gly Gly Thr Glu Met Asp Gly Phe Arg Arg Thr Ile Glu Asn
                325                 330                 335
Gln His Ser Arg Asn Asp Val Met Val Ser Glu Trp Leu Asn Lys Leu
                340                 345                 350
Asn Leu Glu Glu Pro Pro Ser Ser Val Pro Lys Lys Cys Pro Ser Leu
                355                 360                 365
Thr Lys Arg Ser Arg Ala Gln Glu Glu Gln Val Pro Gln Ala Trp Thr
            370                 375                 380
Ala Gly Thr Ser Ser Asp Ser Met Ala Gln Pro Pro Gln Thr Pro Glu
385                 390                 395                 400
Thr Ser Thr Phe Arg Asn Gln Met Pro Ser Pro Thr Ser Thr Gly Thr
                405                 410                 415
Pro Ser Pro Gly Pro Arg Gly Asn Gln Gly Ala Glu Arg Gln Gly Met
                420                 425                 430
Asn Trp Ser Cys Arg Thr Pro Glu Pro Asn Pro Val Thr Gly Arg Pro
            435                 440                 445
Leu Val Asn Ile Tyr Asn Cys Ser Gly Val Gln Val Gly Asp Asn Asn
        450                 455                 460
Tyr Leu Thr Met Gln Gln Thr Thr Ala Leu Pro Thr Trp Gly Leu Ala
465                 470                 475                 480
Pro Ser Gly Lys Gly Arg Gly Leu Gln His Pro Pro Val Gly Ser
                485                 490                 495
Gln Glu Gly Pro Lys Asp Pro Glu Ala Trp Ser Arg Pro Gln Gly Trp
                500                 505                 510
Tyr Asn His Ser Gly Lys
                515

<210> SEQ ID NO 5
<211> LENGTH: 518
<212> TYPE: PRT
<213> ORGANISM: DArtificial Sequence
<220> FEATURE:
<223> OTHER INFORMATION: Dominant Negative Mutant Embodiment

<400> SEQUENCE: 5

Met Ser Cys Val Lys Leu Trp Pro Ser Gly Ala Pro Ala Pro Leu Val
1               5                   10                  15
Ser Ile Glu Glu Leu Glu Asn Gln Glu Leu Val Gly Lys Gly Gly Phe
                20                  25                  30
Gly Thr Val Phe Arg Ala Gln His Arg Lys Trp Gly Tyr Asp Val Ala
            35                  40                  45
Val Arg Ile Val Asn Ser Lys Ala Ile Ser Arg Glu Val Lys Ala Met
        50                  55                  60
Ala Ser Leu Asp Asn Glu Phe Val Leu Arg Leu Glu Gly Val Ile Glu
65                  70                  75                  80
Lys Val Asn Trp Asp Gln Asp Pro Lys Pro Ala Leu Val Thr Lys Phe
                85                  90                  95
Met Glu Asn Gly Ser Leu Ser Gly Leu Leu Gln Ser Gln Cys Pro Arg
```

-continued

```
                100                 105                 110
Pro Trp Pro Leu Leu Cys Arg Leu Leu Lys Glu Val Leu Gly Met
            115                 120                 125
Phe Tyr Leu His Asp Gln Asn Pro Val Leu Leu His Arg Asp Leu Lys
    130                 135                 140
Pro Ser Asn Val Leu Leu Asp Pro Glu Leu His Val Lys Leu Ala Asp
145                 150                 155                 160
Phe Gly Leu Ser Thr Phe Gln Gly Gly Ser Gln Ser Gly Thr Gly Ser
                165                 170                 175
Gly Glu Pro Gly Gly Thr Leu Gly Tyr Leu Ala Pro Glu Leu Phe Val
            180                 185                 190
Asn Val Asn Arg Lys Ala Ser Thr Ala Ser Asp Val Tyr Ser Phe Gly
                195                 200                 205
Ile Leu Met Trp Ala Val Leu Ala Gly Arg Glu Val Glu Leu Pro Thr
            210                 215                 220
Glu Pro Ser Leu Val Tyr Glu Ala Val Cys Asn Arg Gln Asn Arg Pro
225                 230                 235                 240
Ser Leu Ala Glu Leu Pro Gln Ala Gly Pro Glu Thr Pro Gly Leu Glu
                245                 250                 255
Gly Leu Lys Glu Leu Met Gln Leu Cys Trp Ser Ser Glu Pro Lys Asp
            260                 265                 270
Arg Pro Ser Phe Gln Glu Cys Leu Pro Lys Thr Asp Glu Val Phe Gln
        275                 280                 285
Met Val Glu Asn Asn Met Asn Ala Ala Val Ser Thr Val Lys Asp Phe
        290                 295                 300
Leu Ser Gln Leu Arg Ser Ser Asn Arg Arg Phe Ser Ile Pro Glu Ser
305                 310                 315                 320
Gly Gln Gly Gly Thr Glu Met Asp Gly Phe Arg Arg Thr Ile Glu Asn
            325                 330                 335
Gln His Ser Arg Asn Asp Val Met Val Ser Glu Trp Leu Asn Lys Leu
        340                 345                 350
Asn Leu Glu Glu Pro Pro Ser Ser Val Pro Lys Lys Cys Pro Ser Leu
            355                 360                 365
Thr Lys Arg Ser Arg Ala Gln Glu Glu Gln Val Pro Gln Ala Trp Thr
    370                 375                 380
Ala Gly Thr Ser Ser Asp Ser Met Ala Gln Pro Pro Gln Thr Pro Glu
385                 390                 395                 400
Thr Ser Thr Phe Arg Asn Gln Met Pro Ser Pro Thr Ser Thr Gly Thr
                405                 410                 415
Pro Ser Pro Gly Pro Arg Gly Asn Gln Gly Ala Glu Arg Gln Gly Met
            420                 425                 430
Asn Trp Ser Cys Arg Thr Pro Glu Pro Asn Pro Val Thr Gly Arg Pro
        435                 440                 445
Leu Val Asn Ile Tyr Asn Cys Ser Gly Val Gln Val Gly Asp Asn Asn
450                 455                 460
Tyr Leu Thr Met Gln Gln Thr Thr Ala Leu Pro Thr Trp Gly Leu Ala
465                 470                 475                 480
Pro Ser Gly Lys Gly Arg Gly Leu Gln His Pro Pro Val Gly Ser
                485                 490                 495
Gln Glu Gly Pro Lys Asp Pro Glu Ala Trp Ser Arg Pro Gln Gly Trp
            500                 505                 510
Tyr Asn His Ser Gly Lys
            515
```

<210> SEQ ID NO 6
<211> LENGTH: 261
<212> TYPE: PRT
<213> ORGANISM: Artificial Sequence
<220> FEATURE:
<223> OTHER INFORMATION: Kinase Domain

<400> SEQUENCE: 6

```
Leu Glu Asn Gln Glu Leu Val Gly Lys Gly Gly Phe Gly Thr Val Phe
 1               5                  10                  15

Arg Ala Gln His Arg Lys Trp Gly Tyr Asp Val Ala Val Lys Ile Val
             20                  25                  30

Asn Ser Lys Ala Ile Ser Arg Glu Val Lys Ala Met Ala Ser Leu Asp
         35                  40                  45

Asn Glu Phe Val Leu Arg Leu Glu Gly Val Ile Glu Lys Val Asn Trp
     50                  55                  60

Asp Gln Asp Pro Lys Pro Ala Leu Val Thr Lys Phe Met Glu Asn Gly
65                  70                  75                  80

Ser Leu Ser Gly Leu Leu Gln Ser Gln Cys Pro Arg Pro Trp Pro Leu
                 85                  90                  95

Leu Cys Arg Leu Leu Lys Glu Val Val Leu Gly Met Phe Tyr Leu His
            100                 105                 110

Asp Gln Asn Pro Val Leu Leu His Arg Asp Leu Lys Pro Ser Asn Val
        115                 120                 125

Leu Leu Asp Pro Glu Leu His Val Lys Leu Ala Asp Phe Gly Leu Ser
    130                 135                 140

Thr Phe Gln Gly Gly Ser Gln Ser Gly Thr Gly Ser Gly Glu Pro Gly
145                 150                 155                 160

Gly Thr Leu Gly Tyr Leu Ala Pro Glu Leu Phe Val Asn Val Asn Arg
                165                 170                 175

Lys Ala Ser Thr Ala Ser Asp Val Tyr Ser Phe Gly Ile Leu Met Trp
            180                 185                 190

Ala Val Leu Ala Gly Arg Glu Val Glu Leu Pro Thr Glu Pro Ser Leu
        195                 200                 205

Val Tyr Glu Ala Val Cys Asn Arg Gln Asn Arg Pro Ser Leu Ala Glu
    210                 215                 220

Leu Pro Gln Ala Gly Pro Glu Thr Pro Gly Leu Glu Gly Leu Lys Glu
225                 230                 235                 240

Leu Met Gln Leu Cys Trp Ser Ser Glu Pro Lys Asp Arg Pro Ser Phe
                245                 250                 255

Gln Glu Cys Leu Pro
            260
```

<210> SEQ ID NO 7
<211> LENGTH: 240
<212> TYPE: PRT
<213> ORGANISM: Artificial Sequence
<220> FEATURE:
<223> OTHER INFORMATION: Death Domain

<400> SEQUENCE: 7

```
Cys Leu Pro Lys Thr Asp Glu Val Phe Gln Met Val Glu Asn Asn Met
 1               5                  10                  15

Asn Ala Ala Val Ser Thr Val Lys Asp Phe Leu Ser Gln Leu Arg Ser
             20                  25                  30

Ser Asn Arg Arg Phe Ser Ile Pro Glu Ser Gly Gln Gly Gly Thr Glu
```

```
                35                  40                  45
Met Asp Gly Phe Arg Arg Thr Ile Glu Asn Gln His Ser Arg Asn Asp
             50                  55                  60

Val Met Val Ser Glu Trp Leu Asn Lys Leu Asn Leu Glu Glu Pro Pro
 65                  70                  75                  80

Ser Ser Val Pro Lys Lys Cys Pro Ser Leu Thr Lys Arg Ser Arg Ala
                 85                  90                  95

Gln Glu Glu Gln Val Pro Gln Ala Trp Thr Ala Gly Thr Ser Ser Asp
            100                 105                 110

Ser Met Ala Gln Pro Pro Gln Thr Pro Glu Thr Ser Thr Phe Arg Asn
            115                 120                 125

Gln Met Pro Ser Pro Thr Ser Thr Gly Thr Pro Ser Pro Gly Pro Arg
            130                 135                 140

Gly Asn Gln Gly Ala Glu Arg Gln Gly Met Asn Trp Ser Cys Arg Thr
145                 150                 155                 160

Pro Glu Pro Asn Pro Val Thr Gly Arg Pro Leu Val Asn Ile Tyr Asn
                165                 170                 175

Cys Ser Gly Val Gln Val Gly Asp Asn Asn Tyr Leu Thr Met Gln Gln
            180                 185                 190

Thr Thr Ala Leu Pro Thr Trp Gly Leu Ala Pro Ser Gly Lys Gly Arg
            195                 200                 205

Gly Leu Gln His Pro Pro Val Gly Ser Gln Glu Gly Pro Lys Asp
            210                 215                 220

Pro Glu Ala Trp Ser Arg Pro Gln Gly Trp Tyr Asn His Ser Gly Lys
225                 230                 235                 240

<210> SEQ ID NO 8
<211> LENGTH: 420
<212> TYPE: PRT
<213> ORGANISM: Artificial Sequence
<220> FEATURE:
<223> OTHER INFORMATION: Delta Death Domain

<400> SEQUENCE: 8

Met Ser Cys Val Lys Leu Trp Pro Ser Gly Ala Pro Ala Pro Leu Val
 1                   5                  10                  15

Ser Ile Glu Glu Leu Glu Asn Gln Glu Leu Val Gly Lys Gly Gly Phe
                 20                  25                  30

Gly Thr Val Phe Arg Ala Gln His Arg Lys Trp Gly Tyr Asp Val Ala
             35                  40                  45

Val Lys Ile Val Asn Ser Lys Ala Ile Ser Arg Glu Val Lys Ala Met
 50                  55                  60

Ala Ser Leu Asp Asn Glu Phe Val Leu Arg Leu Glu Gly Val Ile Glu
 65                  70                  75                  80

Lys Val Gly Gly Ser Ser Gln Asp Pro Lys Pro Ala Leu Val Thr Lys
                 85                  90                  95

Phe Met Glu Asn Gly Ser Leu Ser Gly Leu Leu Gln Ser Gln Cys Pro
            100                 105                 110

Arg Pro Trp Pro Leu Leu Cys Arg Leu Leu Lys Glu Val Val Leu Gly
            115                 120                 125

Met Phe Tyr Leu His Asp Gln Asn Pro Val Leu Leu His Arg Asp Leu
            130                 135                 140

Lys Pro Ser Asn Val Leu Leu Asp Pro Glu Leu His Val Lys Leu Ala
145                 150                 155                 160

Asp Phe Gly Leu Ser Thr Phe Gln Gly Gly Ser Gln Ser Gly Thr Gly
```

-continued

```
                     165                 170                 175
Ser Gly Glu Pro Gly Gly Thr Leu Gly Tyr Leu Ala Pro Glu Leu Phe
                 180                 185                 190

Val Asn Val Asn Arg Lys Ala Ser Thr Ala Ser Asp Val Tyr Ser Phe
             195                 200                 205

Gly Ile Leu Met Trp Ala Val Leu Ala Gly Arg Glu Val Glu Leu Pro
         210                 215                 220

Thr Glu Pro Ser Leu Val Tyr Glu Ala Val Cys Asn Arg Gln Asn Arg
225                 230                 235                 240

Pro Ser Leu Ala Glu Leu Pro Gln Ala Gly Pro Glu Thr Pro Gly Leu
                245                 250                 255

Glu Gly Leu Lys Glu Leu Met Gln Leu Cys Trp Ser Ser Glu Pro Lys
            260                 265                 270

Asp Arg Pro Ser Phe Gln Glu Cys Leu Pro Lys Thr Asp Glu Val Phe
        275                 280                 285

Gln Met Val Glu Asn Asn Met Asn Ala Ala Val Ser Thr Val Lys Asp
    290                 295                 300

Phe Leu Ser Gln Leu Arg Ser Ser Asn Arg Arg Phe Ser Ile Pro Glu
305                 310                 315                 320

Ser Gly Gln Gly Gly Thr Glu Met Asp Gly Phe Arg Arg Thr Ile Glu
                325                 330                 335

Asn Gln His Ser Arg Asn Asp Val Met Val Ser Glu Trp Leu Asn Lys
            340                 345                 350

Leu Asn Leu Glu Glu Pro Pro Ser Val Pro Lys Lys Cys Pro Ser
        355                 360                 365

Leu Thr Lys Arg Ser Arg Ala Gln Glu Glu Val Pro Gln Ala Trp
    370                 375                 380

Thr Ala Gly Thr Ser Ser Asp Ser Met Ala Gln Pro Pro Gln Thr Pro
385                 390                 395                 400

Glu Thr Ser Thr Phe Arg Asn Gln Met Pro Ser Pro Thr Ser Thr Gly
                405                 410                 415

Thr Pro Ser Pro
            420

<210> SEQ ID NO 9
<211> LENGTH: 518
<212> TYPE: PRT
<213> ORGANISM: Artificial Sequence
<220> FEATURE:
<223> OTHER INFORMATION: Dominant Negative Mutant Embodiment

<400> SEQUENCE: 9

Met Ser Cys Val Lys Leu Trp Pro Ser Gly Ala Pro Ala Pro Leu Val
1               5                  10                  15

Ser Ile Glu Glu Leu Glu Asn Gln Glu Leu Val Gly Lys Gly Gly Phe
            20                  25                  30

Gly Thr Val Phe Arg Ala Gln His Arg Lys Trp Gly Tyr Asp Val Ala
        35                  40                  45

Val Lys Ile Val Asn Ser Lys Ala Ile Ser Arg Glu Val Lys Ala Met
    50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
```

```
                    100             105             110
Pro Trp Pro Leu Leu Cys Arg Leu Leu Lys Glu Val Leu Gly Met
            115             120             125
Phe Tyr Leu His Asp Gln Asn Pro Val Leu Leu His Arg Asp Leu Lys
    130             135             140
Pro Ser Asn Val Leu Leu Asp Pro Glu Leu His Val Lys Leu Ala Asp
145             150             155             160
Phe Gly Leu Ser Thr Phe Gln Gly Gly Ser Gln Ser Gly Thr Gly Ser
                165             170             175
Gly Glu Pro Gly Gly Thr Leu Gly Tyr Leu Ala Pro Glu Leu Phe Val
            180             185             190
Asn Val Asn Arg Lys Ala Ser Thr Ala Ser Asp Val Tyr Ser Phe Gly
            195             200             205
Ile Leu Met Trp Ala Val Leu Ala Gly Arg Glu Val Glu Leu Pro Thr
            210             215             220
Glu Pro Ser Leu Val Tyr Glu Ala Val Cys Asn Arg Gln Asn Arg Pro
225             230             235             240
Ser Leu Ala Glu Leu Pro Gln Ala Gly Pro Glu Thr Pro Gly Leu Glu
                245             250             255
Gly Leu Lys Glu Leu Met Gln Leu Cys Trp Ser Ser Glu Pro Lys Asp
                260             265             270
Arg Pro Ser Phe Gln Glu Cys Leu Pro Lys Thr Asp Glu Val Phe Gln
                275             280             285
Met Val Glu Asn Asn Met Asn Ala Ala Val Ser Thr Val Lys Asp Phe
            290             295             300
Leu Ser Gln Leu Arg Ser Ser Asn Arg Arg Phe Ser Ile Pro Glu Ser
305             310             315             320
Gly Gln Gly Gly Thr Glu Met Asp Gly Phe Arg Arg Thr Ile Glu Asn
                325             330             335
Gln His Ser Arg Asn Asp Val Met Val Ser Glu Trp Leu Asn Lys Leu
                340             345             350
Asn Leu Glu Glu Pro Pro Ser Ser Val Pro Lys Lys Cys Pro Ser Leu
                355             360             365
Thr Lys Arg Ser Arg Ala Gln Glu Glu Gln Val Pro Gln Ala Trp Thr
                370             375             380
Ala Gly Thr Ser Ser Asp Ser Met Ala Gln Pro Pro Gln Thr Pro Glu
385             390             395             400
Thr Ser Thr Phe Arg Asn Gln Met Pro Ser Pro Thr Ser Thr Gly Thr
                405             410             415
Pro Ser Pro Gly Pro Arg Gly Asn Gln Gly Ala Glu Arg Gln Gly Met
                420             425             430
Asn Ala Ser Cys Arg Thr Pro Glu Pro Asn Pro Val Thr Gly Arg Pro
                435             440             445
Leu Val Asn Ile Tyr Asn Cys Ser Gly Val Gln Val Gly Asp Asn Asn
                450             455             460
Tyr Leu Thr Met Gln Gln Thr Thr Ala Leu Pro Thr Ala Gly Leu Ala
465             470             475             480
Pro Ser Gly Lys Gly Arg Gly Leu Gln His Pro Pro Val Gly Ser
                485             490             495
Gln Glu Gly Pro Lys Asp Pro Glu Ala Trp Ser Arg Pro Gln Gly Trp
                500             505             510
Tyr Asn His Ser Gly Lys
                515
```

<210> SEQ ID NO 10
<211> LENGTH: 27
<212> TYPE: DNA
<213> ORGANISM: Artificial Sequence
<220> FEATURE:
<223> OTHER INFORMATION: PCR Primer

<400> SEQUENCE: 10
atcgatatct gcggccgcat gtcgtgc                                    27

<210> SEQ ID NO 11
<211> LENGTH: 27
<212> TYPE: DNA
<213> ORGANISM: Artificial Sequence
<220> FEATURE:
<223> OTHER INFORMATION: PCR Primer

<400> SEQUENCE: 11
cacactggcg gccgttacta gtggatc                                    27

<210> SEQ ID NO 12
<211> LENGTH: 30
<212> TYPE: DNA
<213> ORGANISM: Artificial Sequence
<220> FEATURE:
<223> OTHER INFORMATION: PCR Primer

<400> SEQUENCE: 12
tcccccggga tgtcgtgcgt caagttatgg                                 30

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
tggcttgaga gcccggtgca g                                          21

<210> SEQ ID NO 14
<211> LENGTH: 36
<212> TYPE: DNA
<213> ORGANISM: Artificial Sequence
<220> FEATURE:
<223> OTHER INFORMATION: PCR Primer

<400> SEQUENCE: 14
atcccccggg gcggccgctt atttcccgct atgatt                          36

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
ctgcaccggg ctctcaagcc a                                          21

<210> SEQ ID NO 16
<211> LENGTH: 30
<212> TYPE: DNA
<213> ORGANISM: Artificial Sequence
<220> FEATURE:

```
<223> OTHER INFORMATION: PCR Primer

<400> SEQUENCE: 16
tcccccggga tgtcgtgcgt caagttatgg                              30

<210> SEQ ID NO 17
<211> LENGTH: 36
<212> TYPE: DNA
<213> ORGANISM: Artificial Sequence
<220> FEATURE:
<223> OTHER INFORMATION: PCR Primer

<400> SEQUENCE: 17
atcccccggg gcggccgctt atttcccgct atgatt                       36

<210> SEQ ID NO 18
<211> LENGTH: 30
<212> TYPE: DNA
<213> ORGANISM: Artificial Sequence
<220> FEATURE:
<223> OTHER INFORMATION: PCR Primer

<400> SEQUENCE: 18
tcccccggga tgtcgtgcgt caagttatgg                              30

<210> SEQ ID NO 19
<211> LENGTH: 24
<212> TYPE: DNA
<213> ORGANISM: Artificial Sequence
<220> FEATURE:
<223> OTHER INFORMATION: PCR Primer

<400> SEQUENCE: 19
gtttacgatc ctgaccgcca catc                                    24

<210> SEQ ID NO 20
<211> LENGTH: 36
<212> TYPE: DNA
<213> ORGANISM: Artificial Sequence
<220> FEATURE:
<223> OTHER INFORMATION: PCR Primer

<400> SEQUENCE: 20
atccccgggg gcggccgctt atttcccgct atgatt                       36

<210> SEQ ID NO 21
<211> LENGTH: 23
<212> TYPE: DNA
<213> ORGANISM: Artificial Sequence
<220> FEATURE:
<223> OTHER INFORMATION: PCR Primer

<400> SEQUENCE: 21
gatgtggcgg tcaggatcgt aaa                                     23

<210> SEQ ID NO 22
<211> LENGTH: 30
<212> TYPE: DNA
<213> ORGANISM: Artificial Sequence
<220> FEATURE:
<223> OTHER INFORMATION: PCR Primer

<400> SEQUENCE: 22
tcccccggga tgtcgtgcgt caagttatgg                              30
```

```
<210> SEQ ID NO 23
<211> LENGTH: 36
<212> TYPE: DNA
<213> ORGANISM: Artificial Sequence
<220> FEATURE:
<223> OTHER INFORMATION: PCR Primer

<400> SEQUENCE: 23 atccccggg gcggccgctt atttcccgct atgatt                                    36

<210> SEQ ID NO 24
<211> LENGTH: 37
<212> TYPE: DNA
<213> ORGANISM: Artificial Sequence
<220> FEATURE:
<223> OTHER INFORMATION: PCR Primer

<400> SEQUENCE: 24
aagatatcgc ggccgcatgc caaaaactga tgaagtc                                  37

<210> SEQ ID NO 25
<211> LENGTH: 29
<212> TYPE: DNA
<213> ORGANISM: Artificial Sequence
<220> FEATURE:
<223> OTHER INFORMATION: PCR Primer

<400> SEQUENCE: 25
aggaattctt atttcccgct atgattata                                           29

<210> SEQ ID NO 26
<211> LENGTH: 30
<212> TYPE: DNA
<213> ORGANISM: Artificial Sequence
<220> FEATURE:
<223> OTHER INFORMATION: PCR Primer

<400> SEQUENCE: 26
tcccccggga tgtcgtgcgt caagttatgg                                          30

<210> SEQ ID NO 27
<211> LENGTH: 35
<212> TYPE: DNA
<213> ORGANISM: Artificial Sequence
<220> FEATURE:
<223> OTHER INFORMATION: PCR Primer

<400> SEQUENCE: 27
tcccccgggg cggccgctta aggacttggt gttcc                                    35

<210> SEQ ID NO 28
<211> LENGTH: 30
<212> TYPE: DNA
<213> ORGANISM: Artificial Sequence
<220> FEATURE:
<223> OTHER INFORMATION: PCR Primer

<400> SEQUENCE: 28
tcccccggga tgtcgtgcgt caagttatgg                                          30

<210> SEQ ID NO 29
<211> LENGTH: 21
<212> TYPE: DNA
<213> ORGANISM: Artificial Sequence
<220> FEATURE:
<223> OTHER INFORMATION: PCR Primer
```

-continued

```
<400> SEQUENCE: 29
cctgcaggag gcgttcatgc c                                              21

<210> SEQ ID NO 30
<211> LENGTH: 36
<212> TYPE: DNA
<213> ORGANISM: Artificial Sequence
<220> FEATURE:
<223> OTHER INFORMATION: PCR Primer

<400> SEQUENCE: 30
atccccnggg gcggccgctt atttcccgct atgatt                              36

<210> SEQ ID NO 31
<211> LENGTH: 21
<212> TYPE: DNA
<213> ORGANISM: Artificial Sequence
<220> FEATURE:
<223> OTHER INFORMATION: PCR Primer

<400> SEQUENCE: 31
ggcatgaacg cctcctgcag g                                              21

<210> SEQ ID NO 32
<211> LENGTH: 30
<212> TYPE: DNA
<213> ORGANISM: Artificial Sequence
<220> FEATURE:
<223> OTHER INFORMATION: PCR Primer

<400> SEQUENCE: 32
tcccccggga tgtcgtgcgt caagttatgg                                     30

<210> SEQ ID NO 33
<211> LENGTH: 36
<212> TYPE: DNA
<213> ORGANISM: Artificial Sequence
<220> FEATURE:
<223> OTHER INFORMATION: PCR Primer

<400> SEQUENCE: 33
atccccnggg gcggccgctt atttcccgct atgatt                              36

<210> SEQ ID NO 34
<211> LENGTH: 30
<212> TYPE: DNA
<213> ORGANISM: Artificial Sequence
<220> FEATURE:
<223> OTHER INFORMATION: PCR Primer

<400> SEQUENCE: 34
tcccccggga tgtcgtgcgt caagttatgg                                     30

<210> SEQ ID NO 35
<211> LENGTH: 30
<212> TYPE: DNA
<213> ORGANISM: Artificial Sequence
<220> FEATURE:
<223> OTHER INFORMATION: PCR Primer

<400> SEQUENCE: 35
tcccccggga tgtcgtgcgt caagttatgg                                     30

<210> SEQ ID NO 36
<211> LENGTH: 36
```

-continued

```
<212> TYPE: DNA
<213> ORGANISM: Artificial Sequence
<220> FEATURE:
<223> OTHER INFORMATION: PCR Primer

<400> SEQUENCE: 36
atcccccggg gcggccgctt atttcccgct atgatt                                    36

<210> SEQ ID NO 37
<211> LENGTH: 21
<212> TYPE: DNA
<213> ORGANISM: Artificial Sequence
<220> FEATURE:
<223> OTHER INFORMATION: PCR Primer

<400> SEQUENCE: 37
ttgcccacag ccggcttggc a                                                    21

<210> SEQ ID NO 38
<211> LENGTH: 30
<212> TYPE: DNA
<213> ORGANISM: Artificial Sequence
<220> FEATURE:
<223> OTHER INFORMATION: PCR Primer

<400> SEQUENCE: 38
tcccccggga tgtcgtgcgt caagttatgg                                           30

<210> SEQ ID NO 39
<211> LENGTH: 36
<212> TYPE: DNA
<213> ORGANISM: Artificial Sequence
<220> FEATURE:
<223> OTHER INFORMATION: PCR Primer

<400> SEQUENCE: 39
atcccccggg gcggccgctt atttcccgct atgatt                                    36
```

PROTEIN ACTIVATOR AND APOPTOSIS

This is application is a divisional of application Ser. No. 09/329,418 filed on Jun. 10, 1999, now U.S. Pat. No. 6,096,539, from which applicants claim priority under 35 USC § 120.

FIELD OF THE INVENTION

The present invention relates to nucleic acid and amino acid sequences pertaining to a kinase of death (KOD) biomolecule which is integral to the activation process of cellular apoptosis. Molecular sequences are provided for the design and synthesis of entities that modulate biological and/or pharmacological activity of the native biomolecule. The sequences are also provided for employment to identify compounds that modulate biological and/or pharmacological activity of the native biomolecule. Biologically-effective antisense molecules are provided, as well as dominant negative mutant versions of the kinase of death which are suitable for therapeutic use. The invention is also drawn toward the study, prevention, diagnosis, and treatment of pathophysiological disorders related to apoptosis.

BACKGROUND OF THE INVENTION

Apoptosis, or programmed death at the level of the cell, is needed to orchestrate biological maintenance of the organism during development as well to preserve the normal function and fitness of tissues during a normal life span. Physiological conditions which result from aberrant apoptosis may be dire. Cancer and autoimmune disease may result when there is too little apoptosis, as well as severe stroke damage or the neurodegeneration of Alzheimer's disease when there is too much. Miller, L. J., *Apoptosis, Science*, 281:1 (1998). Apoptotic neuronal cell death appears to be a common denominator of a number of common neurological and psychiatric disorders. Anderson, A. J., et al., A Potential Role for Apoptosis in Neurodegeneration and Alzheimer's Disease, Mol. Neurobiol., 10:19 (1995); W. G. Tatton, et al., Apoptosis in Neurodegenerative Disorders: Potential for Therapy by Modifying Gene Transcription, J. Neural Transm., 49:245 (1997). CNS disorders as well as other disorders wherein apoptosis is believed to contribute to the pathogenesis include the likes of stroke, ischemic injury, Alzheimer's disease, Parkinson's disease, Huntington's Chorea, Amyotrophic Lateral Sclerosis (ALS), hereditary retinal degenerations, glaucoma, cachexia, and spinal muscular atrophy. Apoptosis of glial cells may also contribute to disorders like multiple sclerosis and diabetic peripheral neuropathy.

Apoptosis is known to be involved in the course of a wide variety of developmental processes including normal physiological maturation of the human immune as well as nervous systems. Normal physiological signals activate apoptosis in the context of orderly development in various tissues. Glucocorticoids, withdrawal of cytokines, DNA damage and signals through the antigen receptors of T or B lymphocytes can all induce apoptosis, depending on the inherent susceptibility of each individual cell type. Apoptosis, moreover, has been implicated as an important cellular safeguard against tumorigenesis. Irradiation and chemotherapy are also used artificially to effectively trigger apoptosis for therapeutic purposes. Expression of the natural p53 tumor suppresser gene is required for efficient induction of apoptosis following DNA damage and other physiological damage to the cell. In fact, the cytotoxicity of many commonly used chemotherapeutic agents is mediated by wild-type p53. Moreover, the p53 tumor suppresser gene is frequently mutated in human tumors. The loss of p53 function, and hence compromised apoptosis, may contribute to the clinically significant problem of drug resistant tumor cells emerging following chemotherapy regimens.

Cells have surface sensors termed death receptors which detect and respond to the presence of extracellular death signals by triggering intrinsic apoptosis machinery. These receptors can activate death caspases and within seconds of ligand binding cause an apoptotic demise of the cell. Death receptors belong to the tumor necrosis factor (TNF) receptor gene superfamily, which is defined by similar, cysteine-rich extra cellular domains. The death receptors contain in addition a homologous cytoplasmic sequence termed the "death domain". Death domains typically enable death receptors to engage the cell's apoptotic machinery, but in some instances they mediate functions that are distinct from or even counteract apoptosis. Some molecules that transmit signals from death receptors contain death domains themselves. Ashkenazi, Avi, et al., Death Receptors: Signaling and Modulation, Science, 281:13 (1998). Death receptors have been identified on the surface of cells including the tumor necrosis factor receptor 1 (TNF-R1) and Fas receptor (FasR). The idea of targeting specific death receptors to induce apoptosis in tumors is attractive, because death receptors have direct access to the caspase machinery. Moreover, unlike many chemotherapeutic agents or radiation therapy, death receptors initiate apoptosis independently of the p53 tumor suppressor gene, which is inactivated by mutation in more than half of human cancers. Id.

Cell death via apoptosis is mediated by cysteine proteases, caspases, protein-clipping enzymes, which cleave specifically at aspartic acid, to orchestrate the cell's death program. Once the cascade of caspases have been activated, a series of degradative proteolytic events occur in the cell. In drug-resistant cells, apoptosis fails because of defects in signaling pathways that lead to caspase activation. Therapeutic opportunities are expected to exist by means of bypassing these defects. Death receptors may be activated, for example, resulting in activation of a corresponding initiator caspase. Thornberry, N. A., Caspases: Enemies Within, Science, 281:1312 (1998).

Ligation of the extracellular domain of the cell surface receptor Fas/APO-1 (CD95) elicits a characteristic apoptotic programmed death response in susceptible cells. Stanger, B. Z., et al., RIP: A Novel Protein Containing a Death Domain That Interacts with Fas/APO-1 (CD95) in Yeast and Causes Cell Death, Cell, 81:513 (1995). Stanger et al have identified two gene products that associate with the intracellular domain of Fas: Fas itself, and a 74 Kda protein Receptor Interacting Protein (RIP). RIP contains an N-terminal region with homology to protein kinases and a C-terminal region containing a cytoplasmic motif (death domain) present in the Fas and TNFR1 intracellular domains. Transient overexpression of RIP causes transfected cells to undergo the morphological changes characteristic of apoptosis. Furthermore, the death domain serine/threonine kinase RIP has been demonstrated to interact with the death receptors Fas and tumor necrosis receptor 1 (TNFR1). In vitro, RIP stimulates apoptosis, as well as SAPK/JNK and NF-kB activation. Kelliher, M. A., et al., The Death Domain Kinase RIP Mediates the TNF-Induced NF-kB Signal, Immunity, 8:297 (1998).

Entities which are able to affect the activity of specific biological molecules which activate apoptosis are expected to have significant potential for the ability to control apoptosis as well as disease conditions related thereto.

SUMMARY OF THE INVENTION

The present invention is directed to an isolated and purified polynucleotide molecule comprising a nucleic acid sequence which encodes a polypeptide comprising the sequence as depicted in SEQ ID NO:3 or a variant of SEQ ID NO:3 having at least about 80% homology to a member selected from the group consisting essentially of: (SEQ ID NO:3, SEQ ID NO:6, SEQ ID NO:7, and SEQ ID NO:8).

Isolated and purified polynucleotides of the present invention include but are not limited to sequences comprising SEQ ID NO:1 and SEQ ID NO:2.

The current invention is directed to a purified polypeptide comprising the amino acid sequence as depicted in SEQ ID NO:3 or a variant thereof as defined herein.

A preferred embodiment of the invention is an isolated and purified biologically effective antisense polynucleotide molecule comprising an oligomer in the range from about 12 to about 25 nucleotides in length which is complementary to a region within positions about 150–230 of SEQ ID NO:1.

The present invention is also directed to an isolated and purified polynucleotide molecule comprising a nucleic acid sequence which encodes a biologically effective dominant negative mutant variant of SEQ ID NO:3 which has the ability to modulate the biological and/or pharmacological activity of the apoptosis activator of the present invention. A further preferred embodiment of the invention is a biologically effective dominant negative mutant polypeptide variant of SEQ ID NO:3.

The instant invention is further directed to methods of identifying compounds that modulate a biological and/or pharmacological activity of a protein which mediates apoptosis, which comprise:

(a) combining a candidate compound modulator with a polypeptide derived from the SEQ ID NO:3 apoptosis activator, and (b) measuring an effect of the candidate compound modulator on the biological and/or pharmacological activity of the polypeptide.

The present invention is also directed to compounds identified by means of the aforementioned method, wherein said compound modulates a biological and/or pharmacological activity of a protein which mediates apoptosis.

Additionally, the invention is directed to methods of treatment of a patient in need of such treatment for a dysfunctional apoptosis condition, comprising administering: (a) an effective amount of a compound which modulates a biological and/or pharmacological activity of a protein which mediates apoptosis; and/or (b) an effective amount of a polynucleotide which encodes a biologically effective dominant negative mutant derived from SEQ ID NO:3; and/or (c) an effective amount of a biologically effective antisense molecule derived from the complement of SEQ ID NO: 1.

The current invention is also drawn toward an antibody specific for a purified polypeptide comprising the amino acid sequence as depicted in SEQ ID NO:3, as well as a diagnostic composition comprising the antibody for the identification of a polypeptide sequence comprising the amino acid sequence substantially as shown in SEQ ID NO:3.

The invention is also directed to PCR primers derived from SEQ ID NO:1.

DETAILED DESCRIPTION OF THE INVENTION

Figure 1:
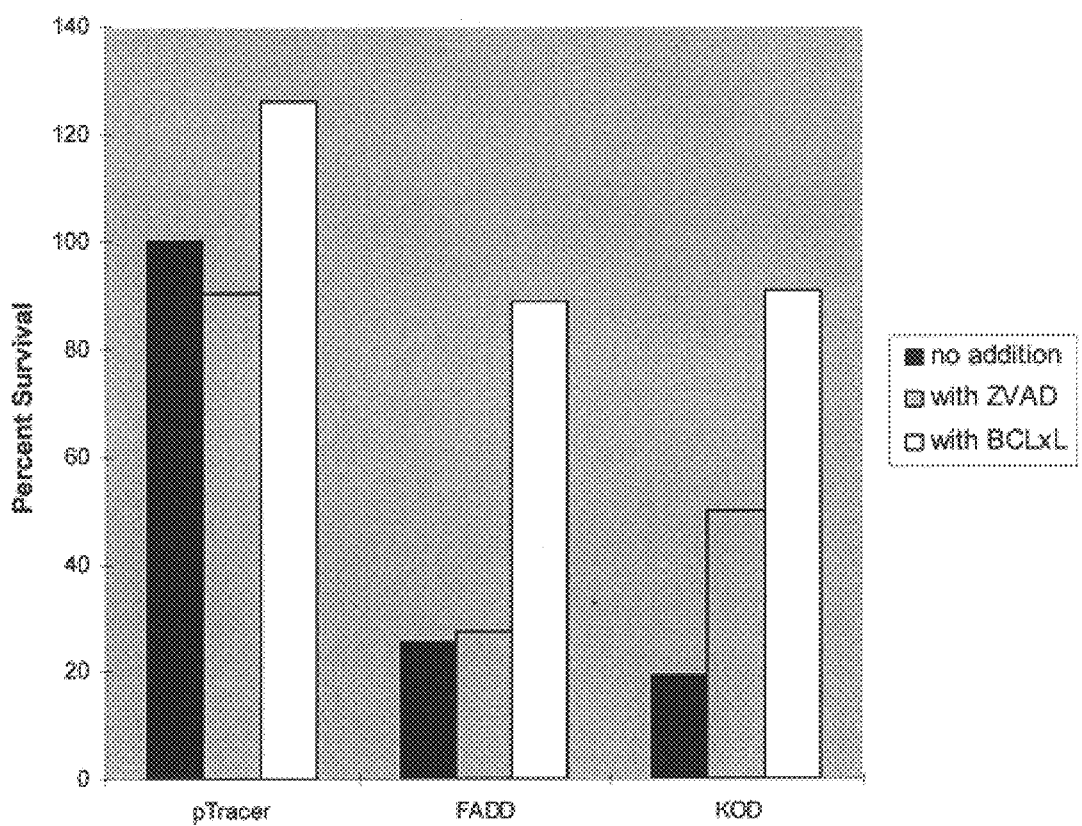
FIG. 1 shows a graph which demonstrates KOD's effects on apoptosis. The activator of apoptosis was transfected into cells along with other modulators of apoptosis.

Unless defined otherwise, all technical and scientific terms used herein have the same meaning as is commonly understood by one of skill in the art to which this invention belongs. All publications and patents referred to herein are incorporated by reference.

Biological activity as used herein in reference to the protein activator of apoptosis of the present invention refers to the ability of the biomolecule to perfom any one or more of the functions including but not limited to the ability to autophosphorylate, to phosphorylate a substrate, to bind ATP, to bind or interact with CRADD, RAIDD, TRADD, SODD, TNF-R1, TRAF2, FasR, DR3, DR4 and/or DR5.

Pharmacological activity as used herein in reference to the protein activator of apoptosis of the present invention refers to the ability to mediate apoptosis or cell death and/or the ability to activate of one or more transcription factors, or activate a signal transduction molecule or terminal kinase, and/or the direct or indirect transcriptional activation of one or more genes.

Dominant negative mutant as used herein refers to a polypeptide or a nucleic acid coding region sequence which has been changed with regard to at least one position in the sequence, relative to the corresponding wild type native version at a position which changes an amino acid residue position at an active site required for biological and/or pharmacological activity of the native peptide. Accordingly, dominant negative mutants of SEQ ID NO:3 contemplated herein include, but are not limited to, polypeptide species which manifest any change (substitution and/or deletion) with regard to at least one amino acid in the following SEQ ID NO:3 positions: 50 (lysine), and/or 143 (aspartic acid), and/or tryptophans at 435 and/or 478. Dominant negative mutant embodiments of the invention are moreover nucleic acids which encode peptides, as well as the peptides themselves, which comprise fragments of SEQ ID NO:3, i.e., SEQ ID NO:6, SEQ ID NO:7, and SEQ ID NO:8, which have one or more of the same positions, corresponding to SEQ ID NO:3 (positions: 50 (lysine), and/or 143 (aspartic acid), and/or tryptophans at 435 and/or 478), changed (substitution and/or deletion).

Biologically effective as used herein in reference to antisense nucleic acid molecules as well as dominant negative mutant nucleic acid coding regions and dominant negative mutant peptides refers to the ability of these molecules to modulate the biological and/or pharmacological activity of the apoptosis activator (KOD) of the present invention, including direct or indirect modulation of transcriptional activation of one or more genes, and/or transcription/translation of nucleic acid coding regions of the protein of the present invention. Biologically effective antisense molecules as well as nucleic acids which encode biologically effective dominant negative mutant versions of SEQ ID NO:3, or derivatives thereof, are preferred embodiments of the present invention.

As depicted as used herein refers the sequence as well as inherent derivatives thereof, e.g., functional derivative that demonstrate or perform substantially the same biological and/or pharmacological activity in substantially the same way. 'As depicted' is therefore intended to encompass biologically and/or pharmacologically active truncated versions clearly derived from the sequences disclosed and characterized herein (e.g., evidenced domains) as well as chimeric sequences which contain one or more of them.

Variant as used herein refers to sequences substantially as shown having changes, e.g., a polypeptide sequence comprising a sequence which differs from the sequence referred to by at least one amino acid substitution, addition, or deletion, preferrably a conservative amino acid substitution, that demonstrate or perform substantially the same biological and/or pharmacological activity in substantially the same way, as well as truncated versions of these variants. However, variant as used herein is intended to encompass all contemplated biologically effective dominant negative mutants, several species of which are set forth herein.

The term modulation is used herein to refer to the capacity to either enhance or inhibit a function of a biological molecule including, but not limited to, a biological and/or pharmacological activity of a signal transduction molecule, or to the capacity to either enhance or inhibit a functional property of a nucleic acid coding region. Modulate physiology as used herein refers to the biophysiological regulation of cells and/or tissue and the treatment of pathophysiological disorders related thereto.

Direct administration as used herein refers to the direct administration of nucleic acid molecules, peptides, or compounds as well as contemplated derivatives/variants of the present invention. Direct administration includes but is not limited to ex vivo as well as in vivo gene therapy techniques.

Purified as used herein refers to molecules, either nucleic acid or amino acid sequences, that are removed from their natural environment and isolated or separated from at least one other component with which they are naturally associated.

Expression vector as used herein refers to nucleic acid vector constructions to direct the transcription of nucleic acid regions in host cells. Expression vectors include but are not limited to plasmids, retroviral vectors, viral and synthetic vectors.

Transformed host cells as used herein refer to cells which harbor one or more nucleic acids of the present invention.

Apoptosis

Apoptosis, although vital to life, can go awry and thereby mediate severe pathophysiological conditions. For example, upon blockage of the blood supply to part of the brain, as in a stroke, neurons in the most severely affected area die immediately from oxygen starvation, known as ischemia. A gradual loss of neurons in the region outside the stroke's core, where the oxygen supply is reduced but not eliminated is furthermore common to stroke victims. Recent experiments in rats and mice suggest that some cells that might otherwise recover from the ischemia may be dying because the injury triggers their suicide programs. Accordingly, cell death is viewed as a good target, for example, for therapeutic drugs aimed at limiting stroke damage. Barinaga, M., The Stroke-Damaged Neurons May Commit Cellular Suicide, Science, 281:1302 (1998). Moreover, caspases are intracellular proteases that function as initiators and effectors of apoptosis that can be directly regulated by protein phosphorylation. Cardone, M. H., et al., Regulation of Cell Death Protease Caspase-9 by Phosphorylation, Science, 282:1318 (1998). Agonists of apoptosis are expected to be valuable for the prevention and/or treatment, for example, of cancer and/or autoimmune disease where induction of apoptosis is desirable. Antagonsits or inhibitors are expected to be valuable for the prevention and/or treatment of disorders where apoptosis is not desirable, such as stroke, neurodegenerative diseases, Alzheimer's disease, ALS, spinal muscular atrophy, Huntington's Chorea and Parkinson's Disease. See, e.g., Adams, J. M., Science, 281:1322 (1998).

RIP

Stanger et al found that overexpression of RIP results in the induction of a cell death program morphologically similar to apoptosis. Deletion of the C-terminal region of RIP spanning the segment of death domain homology eliminated the apoptotic response, but deletion of the kinase domain did not entirely quench activity. Cell, 81:513 (1995). RIP protein consists of three domains: an N-terminal kinase domain, an a-helical intermediate domain and a C-terminal death domain. RIP is unique among the known death domain proteins in that it contains an active serine/threonine kinase domain capable of autophosphorylation. Kelliher, M. A., et al., Immunity, 8:297 (1998).

RIP interacts via its death domain with the death domain adapter protein TRADD (TNFR1-associated death domain protein). This interaction is TNF dependent. Hsu, H., et al., The TNF Receptor 1-Associated Protein TRADD Signals Cell Death and NF-Kb Activation, Cell 81:495 (1995); Hsu, H., et al., TRADD-TRAF2 and TRADD-FADD Interactions Define Two Distinct TNF Receptor Signal Transduction Pathways, Cell, 84:299 (1996). The RIP death domain also binds RAIDD (RIP-associated ICH1/CED3-homologous protein with a death domain). Duan, H., et al., RAIDD is a New Death Adaptor Molecule, Nature, 385:86 (1997). Hence, RIP is implicated in directly linking the TNFR1 complex to the ICE/caspase cascade. Kelliher, M. A., et al., Immunity, 8:297 (1998).

TRADD functions as a platform adapter that recruits several signaling molecules to the activated receptor. RAIDD or CRADD binds through a death domain to the death domain of RIP and through a CARD motif to a similar sequence in the death effector caspase-2, thereby inducing apoptosis. Ashkenazi, Avi, et al., Death Receptors: Signaling and Modulation, Science, 281:13 (1998); Hsu, H. et al., Cell, 81:495 (1995); Duan, H., et al., Nature, 385:86 (1997); Ahmad, M., et al., Cancer Res., 57:615 (1997).

Silencer of death domains (SODD), a widely expressed 60-kilodalton protein was recently found to be associated with the death domain of TNF-R1. TNF treatment was demonstrated to release SODD from TNF-R1, permitting the recruitment of proteins such as TRADD and TRAF2 to the active TNF-R1 signaling complex. SODD was also also demonstrated to interact with death receptor-3 (DR3), another member of the TNF receptor superfamily. Thus, SODD association may be representative of a general mechanism for preventing spontaneous signaling by death domain-containing receptors. Jiang, Y., et al., Prevention of Constitutive TNF Receptor 1 Signaling by Silencer of Death Domains, Science, 283:543 (1999). In addition to TNF-R1, several other members of the TNF receptor superfamily, including Fas, DR3, DR4 and DR5, contain intracellular death domains and are capable of triggering apoptosis when activated by their respective ligands. The death domains of these receptors can self-associate and bind other death domain-containing proteins, demonstrating that death domains function as protein-protein interaction domains. Id.

All RIP mutants containing the C-terminal death domain are capable of inducing cell death when overexpressed, demonstrating that the death domain is both necessary and sufficient for apoptosis. Thus, the kinase and intermediate domains of RIP are involved in activation of NF-kB and TRAF2 binding, whereas the RIP death domain associates with TRADD and other death domain proteins to elicit the apoptotic response. In addition to the postnatal lethality, RIP-deficient mice exhibit extensive apoptosis in the lymphoid and adipose tissues, illustrating a role that that RIP functions in vivo to suppress cell death. Kelliher, M. A., et al., Immunity, 8:297 (1998).

Novel Human Protein Activator of Apoptosis or Kinase of Death

SEQ ID NO:1 is the 1873 base nucleotide sequence of the full-length cDNA pertaining to the protein activator of apoptosis or kinase of death (KOD) disclosed herein. SEQ ID NO:2 is the 1557 base structural coding region. SEQ ID NO:3 is the 518 amino acid residue sequence of the 57kD KOD protein activator of apoptosis.

An important feature of SEQ ID NO:3 this sequence is exemplified by positions 21–281 (SEQ ID NO:6), for example, which contain the signatures of a kinase. The carboxyl portion of the KOD protein, SEQ ID NO:3, contains a death domain. The kinase/death domain combination was previously exemplified in the known human regulator of apoptosis, RIP. Stanger, B. Z., et al., RIP: A Novel Protein Containing a Death Domain That Interacts with Fas/APO-1 (CD95) in Yeast and Causes Cell Death, Cell, 81:513 (1995). Kelliher, M. A., et al., The Death Domain Kinase RIP Mediates the TNF-Induced NF-kB Signal, Immunity, 8:297 (1998).

As described herein when KOD is overexpressed in HeLa cells, 80–95% of the cells die by apoptosis. By contrast, nearly 100% of cells transfected with the control vector only, survive. See, FIG. 1; Example III. FADD is used as a positive control in this case and is known to induce apoptosis. Chinnaiyan, A. M., et al., Cell, 81(4):505 (1995). When BCL-xL (a suppressor of apoptosis) is co-transfected with KOD into HeLa cells, the cells are rescued from death. See, Boise, L. H., et al., Cell, 74(4):597 (1993). Hence KOD is a positive activator of apoptosis. KOD induced apoptosis is also blocked by ZVAD (an inhibitor of caspase-dependent apoptosis). See, Garcia-Calvo, M., et al., J. Biol. Chem., 273(49):32608 (1998).

Conditions for an assay of survival 48 hours post-transfection are the same as used in the apoptosis assay described in Example III (Bax and FADD are positive controls for cell killing). KOD (SEQ ID NO:3) kills cells with about the same efficiency as the positive controls. Destruction of the kinase active site (SEQ ID NO:4) or ATP binding site (SEQ ID NO:5) or removal of the whole kinase domain (SEQ ID NO:7) has no effect on the killing rate. However, loss of the death domain (e.g., SEQ ID NO:8) removes the killing activity for SEQ ID NO:3. The SEQ ID NO:9 mutant is the most effective at destroying the pharmacological (apoptotic acivation) activity of KOD. See, Examples IX–XIV.

KOD expression, upon Northern analyses, appears to be most prominent in tumor tissue of the colon, breast and lung and is absent or present only at low levels in tissues such as normal colon, normal breast, normal lung. See, Example IV.

The data presented demonstrates that KOD is a positive regulator of apoptosis. Current literature suggests that inappropriate induction of apoptosis, for example, is a component of the pathophysiology of chronic neurological disorders. See, e.g., Science, 281:1301 (1998); Dragunow, M., et al., Reviews in the Neurosciences, 8:223 (1998); Stanfanis, L., Current Opions in Neurology, 10:299 (1997). Antagonsits or inhibitors are expected to be valuable for the prevention and/or treatment of disorders where apoptosis is not desirable, such as stroke, neurodegenerative diseases, Alzheimer's disease, ALS, spinal muscular atrophy, Huntington's Chorea and Parkinson's Disease. Agonists of apoptosis are expected to be valuable for the prevention and/or treatment, for example, of cancer and/or autoimmune disease where induction of apoptosis is desirable. See, e.g., Adams, J. M., Science, 281:1322 (1998).

Significant evidence has been provided that apoptosis is responsible for biological effects across a wide variety of disease areas. Accordingly, molecules which mediate or activate apoptosis are viewed as excellent targets, for example, for therapeutic drugs aimed at controllong disease manifested by dysfunctinal apoptosis. Therefore the KOD activator of apoptosis molecule described herein, SEQ ID NO:3, or nucleic acid sequences coding therefor, e.g. SEQ ID NO:1 and/or SEQ ID NO:2, have significant potential for the ablity attenuate pathophysiological responses. The ability to screen for antagonists and/or agonists which modulate the biological and/or pharmacological activity of the native KOD is significantly valuable toward the identification and development of therapeutic agents. Moreover, diagnostic applications are readily apparent for the detection of pathophysiological conditions manifested by abnormal levels of molecules such as SEQ ID NO:2 and/or SEQ ID NO:3 by means of PCR sequence amplification and subsequent detection and/or antibody based assays, e.g., ELISA-based assays, which are well-known to those skilled in the art and readily performed provided the information disclosed herein.

The present invention relates to nucleic acid sequences and amino acid sequences of the KOD and variants thereof and to the use of these sequences to identify compounds that modulate the biological and/or pharmacological activity of a native mediator of apoptosis.

Polynucleotide sequences which encode the KOD molecule as depicted in SEQ ID NO:3 and variants thereof contemplated herein are particularly preferred embodiment of the present invention. Biologically effective antisense molecules and nucleic acids which encode biologically effective dominant negative mutant versions of SEQ ID NO:3, or derivatives thereof, as well as dominant negative mutant versions of SEQ ID NO:3, and derivatives thereof, examples of each of which are described infra, are preferred embodiments of the present invention and are intended to fall within the scope of the claims appended hereto.

The present invention also provides a method of treatment for a patient in need of such treatment, videlicet for a patient who suffers a pathological condition manifested by dysfunctional apoptosis or a condition which is mediated by the SEQ ID NO:3 KOD, or another molecule which mediates apoptosis, or a downstream transcriptional activator, comprising administering an effective amount of a biologically effective antisense nucleic acid molecule derived from SEQ ID NO:1; or administering an effective amount of a nucleic acid which encodes a biologically effective dominant negative mutant version of the KOD; or administering a compound that modulates the biological and/or pharmacological activity of SEQ ID NO:3 which was identified by a method described herein.

The present invention relates to nucleic acid sequences (e.g., SEQ ID NO:1 and SEQ ID NO:2) and amino acid sequences (e.g., SEQ ID NO:3, SEQ ID NO:6, SEQ ID NO:7, and SEQ ID NO:8) of the human activator of apoptosis as well as inherent derivatives thereof, e.g., functional derivative that demonstrate or perform substantially the same biological and/or pharmacological activity in substantially the same way. The invention is also intended to encompass biologically and/or pharmacologically active truncated versions clearly derived from the sequences disclosed and characterized herein (e.g., evidenced domains described infra) as well as chimeric sequences which contain one or more of them.

Variants

The present invention relates to variants of nucleic acid sequences sequences (e.g., SEQ ID NO:1 and SEQ ID NO:2) and amino acid sequences (e.g., SEQ ID NO:3) substantially as shown, which have changes, e.g., a polypeptide sequence comprising a sequence which differs from the sequence referred to by at least one amino acid substitution, preferably a conservative amino acid substitution, that demonstrate or perform substantially the same biological and/or pharmacological activity in substantially the same way, as well as molecules which comprise truncated versions of these variants (e.g., SEQ ID NO:6, SEQ ID NO:7, and SEQ ID NO:8). However, variant as used herein is intended to encompass all contemplated biologically effective dominant negative mutants, several species of which are set forth herein.

A preferred variant, as depicted in SEQ ID NO:3 for instance, is one having at least 80% amino acid sequence homology (identity) to SEQ ID NO:3 or a biologically and/or pharmacologically active substantial fragment thereof (e.g., SEQ ID NO:6, SEQ ID NO:7, or SEQ ID NO:8); a more preferred variant is one having at least 90% amino acid sequence homology; and a most preferred variant is one having at least 95% amino acid sequence homology to the KOD amino acid sequence as depicted in SEQ ID NO:3 or a biologically and/or pharmacologically active substantial fragment thereof (e.g., SEQ ID NO:6, SEQ ID NO:7, or SEQ ID NO:8). Variants within the scope of this invention also include biologically-effective dominant negative mutants of these contemplated embodiments.

A variant of the activator of apoptosis, e.g., SEQ ID NO:3, of the present invention may have an amino acid sequence that is different by one or more amino acid substitutions. Embodiments which comprise amino acid deletions and/or additions are also contemplated. The variant may have conservative changes (amino acid similarity), wherein a substituted amine acid has similar structural or chemical properties, for example, the replacement of leucine with isolcucine. A variant may have nonconservative changes, e.g., replacement of a glycine with a tryptophan. Embodiments within the intended scope of the invention also include SEQ ID NO:3, SEQ ID NO:6, SEQ ID NO:7, and SEQ ID NO:8 having one or more amino acid deletions or insertions, or both. Guidance in determining which and how many amino acid residues may be substituted, inserted or deleted without abolishing biological or proposed pharmacological activity may be reasonably inferred in view of this disclosure and may be further be found using computer programs well known in the art, for example, DNAStar software.

Amino acid substitutions may be made, for instance, on the basis of similarity in polarity, charge, solubility, hydrophobicity, hydrophilicity, and/or the amphipathic nature of the residues as long as a biological and/or pharmacological activity of the native molecule is retained. However, amino acid substitutions are important to construct contemplated biologically effective dominant negative mutants, several species of which are set forth herein.

Negatively charged amino acids, for example, include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine. However, in the construction of biologically effective dominant negative mutants at least one amino acid residue position at an active site required for biological and/or pharmacological activity in the native peptide is changed to produce an agent or entity having reduced activity or which is devoid of detectable native wild type activity.

Suitable substitutions of amino acids include the use of a chemically derivatized residue in place of a non-derivatized residue. D-isomers as well as other known derivatives may also be substituted for the naturally occurring amino acids. See, e.g., U.S. Pat. No. 5,652,369, Amino Acid Derivatives, issued Jul. 29, 1997. Example substitutions are set forth in TABLE 1 as follows:

TABLE 1

| Original residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences are aligned so that the highest order homology (match) is obtained. "Identity" per se has an art-recognized meaning and can be calculated using published techniques. Computer program methods to determine identity between two sequences, for example, include DNAStar software (DNAStar Inc., Madison, Wis.); the GCG program package (Devereux, J., et al., Nucleic Acids Research (1984) 12(1):387); BLASTP, BLASTN, FASTA (Atschul, S. F. et al., J Molec Biol (1990) 215:403). Homology (identity) as defined herein is determined conventionally using the well known computer program, BEST-FIT (Wisconsin Sequence Analysis Package, Version 8 for Unix, Genetics Computer Group, University Research Park, 575 Science Drive, Madison, Wis. 53711). When using BESTFIT or any other sequence alignment program to determine whether a particular sequence is, for example, about 80% homologous to a reference sequence, according to the present invention, the parameters are set such that the percentage of identity is calculated over the full length of the reference nucleotide sequence or amino acid sequence and that gaps in homology of up to about 20% of the total number of nucleotides in the reference sequence are allowed. Eighty percent of homology is therefore determined, for example, using the BESTFIT program with parameters set such that the percentage of identity is calculated over the full length of the reference sequence, e.g., SEQ ID NO:3, and gaps of up to 20% of the total number of amino acids in the reference sequence are allowed, and wherein up to 20% of the amino acid residues in the reference sequence may be deleted or substituted with another amino acid, or a number of amino acids up to 20% of the total amino acid residues in the reference sequence may be inserted into the reference sequence. Percent homologies are likewise determined, for example, to identify preferred species, within the scope of the claims appended hereto, which reside within the range of about 80 percent to 100 percent homology to SEQ ID NO:3 as well as biologically and/or pharmacologically active functional derivatives thereof and biologically effective dominant negative mutants contemplated herein.

Percentage similarity (conservative substitutions) between two polypeptides may also be scored by comparing the amino acid sequences of the two polypeptides by using programs well known in the art, including the BESTFIT program, by employing default settings for determining similarity.

The present invention relates, in part, to the inclusion of the polynucleotide encoding KOD in an expression vector which can be used to transform host cells or organisms. Such transgenic hosts are useful for the production of the activator of apoptosis as well as valuable variations thereof contemplated herein.

The nucleic acid sequence also provides for the design of antisense molecules, example embodiments of which are provided herein, which are useful in downregulating, diminishing, or eliminating expression, e.g., transcription and/or translation of sequences which comprise SEQ ID NO:2 in cells.

The human signal-transduction kinase molecule of the present invention is used in screening assays to identify antagonists or inhibitors which bind to, or interact with, the activator of apoptosis, emulate its substrate, or otherwise inactivate the biomolecule or compete biologically, e.g., competitive interaction or competitive binding inhibition, with the native SEQ ID NO:3 biomolecule. KOD, as well as derivatives contemplated herein are used in screening assays to identify agonists which agonize or mimic the biological and/or pharmacological activity, induce the production of or prolong the biological halflife of the molecule in vivo or in vitro.

The invention also relates to pharmaceutical compositions which comprise molecules as depicted in SEQ ID NO:2 or SEQ ID NO:3 or variants of these molecules as defined herein for the treatment of pathological disorders related to or mediated by the human activator of apoptosis of the present invention.

Example Embodiments and Dominant Negative Mutants

A purified polynucleotide is preferred which comprises a nucleic acid sequence which encodes a polypeptide comprising the sequence as depicted in SEQ ID NO:3 or a variant of SEQ ID NO:3, including but not limited to SEQ ID NO:4, SEQ ID NO:5, SEQ ID NO:6, SEQ ID NO:7, SEQ ID NO:8 and SEQ ID NO:9.

The KOD (SEQ ID NO:3) coding region, SEQ ID NO:2, can be obtained from existing cDNA (e.g., ORIGENE (Rockville, Md.) or other suitable cDNA source, for example, by PCR amplification using primers, e.g. SEQ ID NO:10 and SEQ ID NO:11, as described in Example I. SEQ ID NO:2, for example, (as well as variations thereof) may be inserted into expression vectors, with or without fusion protein "tags", for expression of a protein, e.g., SEQ ID NO:3, which can be purified and screened for biological and/or pharmacological activity, including mediation of apopotosis (cell death) for example as described in the Examples appended hereto. Prokaryotic expression vectors may be used including the likes of, for example, pGEX (GST fusion), pET (+/− His$_6$ or T7 tag), as well as eukaryotic expression vectors including the likes of, for example, pcDNA3.1His, pIRES-EGFP, pcDNA3, and pEBVHis. Recombinant proteins, derived from SEQ ID NO:3, are provided for use in screening assays for the identification of compounds which may modulate the biological and/or pharmacological activity of biological molecules, e.g. KOD, which mediate apoptosis.

An example dominant negative mutant embodiment of SEQ ID NO:3 (aspartic acid at position 143 changed to alanine) is set forth in SEQ ID NO:4. See Example X.

SEQ ID NO:5 is a further example dominant negative mutant of SEQ ID NO:3 wherein lysine at position 50 (in the ATP binding site) is changed to arginine. See Example XI.

SEQ ID NO:9 is another example dominant negative mutant of SEQ ID NO:3 wherein tryptophans at position 435 and 478 are both changed to alanine. See Example XIV.

The following embodiments are preferred: A purified polynucleotide comprising a nucleic acid sequence which encodes a polypeptide having at least about 80% homology to a member selected from the group consisting essentially of: (SEQ ID NO:3, SEQ ID NO:6, SEQ ID NO:7, and SEQ ID NO:8). A purified polynucleotide comprising a nucleic acid sequence which encodes a polypeptide comprising the sequence selected from the group consisting of SEQ ID NO:3 or a fragment of SEQ ID NO:3 (e.g., SEQ ID NO:6, SEQ ID NO:7, SEQ ID NO:8 ) wherein one or more of the following positions corresponding to SEQ ID NO:3 are substituted or deleted: (position 143 (aspartic acid); position 50 (lysine); position 435 (tryptophan); and position 478 (tryptophan)).

Pharmacologically significant embodiments of the invention are peptides which comprise the kinase domain of the activator of apoptosis, e.g., SEQ ID NO:6 (SEQ ID NO:3 positions 21–281 or an effective portion thereof), as well as polynucleotides which comprise a nucleic acid sequence which encodes SEQ ID NO:6 or an effective portion thereof. Embodiments are also contemplated wherein positions 50 (lysine), and/or position 143 (aspartic acid) of this kinase domain example (e.g., SEQ ID NO:3 positions 21–281 or an effective portion thereof) are substituted or deleted to create pharmacologically significant dominant negative mutant versions, as well as polynucleotides which comprise a nucleic acid sequence which encode these peptides.

Further example pharmacologically significant embodiments of the current invention are peptides which comprise the death domain of the activator of apoptosis, e.g., SEQ ID NO:7 (SEQ ID NO:3 positions 280–518 or an effective portion thereof), as well as polynucleotides which comprise a nucleic acid sequence which encodes SEQ ID NO:7 or an effective portion thereof. Embodiments are also contemplated wherein positions 435 (tryptophan); and/or position 478 (tryptophan)) of this death domain example (e.g., SEQ ID NO:3 positions 280–518 or an effective portion thereof) are substituted or deleted to create pharmacologically significant dominant negative mutant versions, as well as polynucleotides which comprise a nucleic acid sequence which encode these peptides.

Antisense Molecules

Various nucleic acid sequences complementary to SEQ ID NO:1 and/or SEQ ID NO:2 are used in another embodiment of the invention to modulate activation of apoptosis by affecting gene expression, e.g., transcription and/or translation of the subject sequences, in cells. Pharmacological activity of an endogenous gene may be modulated by affecting the transcription and/or translation, for example, of the endogenous gene by use or administration of anti-sense constructs to produce anti-sense transcripts or by direct delivery of anti-sense oligomers. Antisense constructs and oligomers may each be used as embodiments of the present invention and each are related to therapeutic method embodiments practiced via direct administration as defined herein. Translation is most effectively inhibited by blocking the mRNA at a site at or near the initiation codon. Thus, oligonucleotides complementary to the 5'-terminal region of the GTPase effector kinase mRNA transcript are preferred.

Antisense molecules which comprise oligomers in the range from about 12 to about 25 nucleotides which are complementary the regions of SEQ ID NO:1 and/or 5' region pSEQ ID NO:2 which are proximal to, or include, the translational start codon, or a portion thereof, are preferred embodiments of the invention. Antisense molecules comprising oligomers from about 12 to about 25 nucleotides in length which are complementary to a region within the SEQ ID NO:1 positions 150–230 are particularly preferred embodiments. Oligonucleotides which comprise sequences complementary to the following positions of SEQ ID NO:1 are example embodiments of the invention: SEQ ID NO:1 positions 150–162; 153–165; 155–167; 157–169; 158–170; 159–171; 160–172; 161–173; 162–174; 163–175; 164–176; 165–177; 166–178; 167–179; 168–180; 169–181; 170–182; 171–183; 172–184; 173–185; 174–186; 175–187; 176–188; 177–189; 178–190; 179–191; 180–192; 181–193; 182–194; 183–195; 184–196; 185–197; 186–198; 187–199; 188–200; 189–201; 190–202; 191–203; 192–204; 193–205; 194–206; 195–207; 196–208; 197–209; 198–210; 199–211; 200–212; 201–213; 202–214; 203–215; 204–216; 205–217; 206–218; 207–219; 208–220; 209–221; 210–222; 211–223; 212–224; 213–225; 214–226; 216–228; and 218–230.

Oligonucleotides which comprise sequences complementary to and hybridizable to the recited area of the KOD mRNA are contemplated for therapeutic use. U.S. Pat. No. 5,639,595, Identification of Novel Drugs and Reagents, issued Jun. 17, 1997, wherein methods of identifying oligonucleotide sequences that display in viva activity are thoroughly described, is herein incorporated by reference.

Nucleotide sequences that are complementary to the KOD-encoding nucleic acid sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, Hybrid Oligonucleotide Phosphorothioates, issued Jul. 29, 1997, and U.S. Pat. No. 5,652,356, Inverted Chimeric and Hybrid Oligonucleotides, issued Jul. 29, 1997, which describe the synthesis and effect of physiologically-stable antisense molecules, are incorporated by reference. Signal-transduction GTPase effector kinase antisense molecules may be introduced into cells by microinjection, liposome encapsulation or by expression from vectors harboring the antisense sequence. Antisense therapy may be particularly useful for the treatment of diseases where it is beneficial to reduce the biological and/or pharmacological activity of the activator of apoptosis, KOD.

Gene Therapy

Embodiments of biological molecules which mediate apoptosis described herein, i.e., nucleic acids or dominant negative mutant versions thereof as well as antisense embodiments may be administered to a subject via gene therapy to modulate, i.e., boost or attenuate the corresponding biological and/or pharmacological activity or gene expression of an endogenous molecule which mediates apoptosis. Nucleic acid sequences of the present invention may be delivered ex vivo or in vivo to the cells of target organs in a tissue-specific manner. The KOD coding region as well as variants thereof contemplated herein can be ligated into viral vectors which mediate transfer of the KOD nucleic acid coding regions by infection of recipient host cells. Suitable viral vectors include retrovirus, adenovirus, adeno-associated virus, herpes virus, vaccinia virus, polio virus and the like. See, e.g., U.S. Pat. No. 5,624,820, Episomal Expression Vectorfor Human Gene Therapy, issued Apr. 29, 1997. GENOVO Corporation, for instance, Sharon Hill, Pa., at the date of this application, have a readily commercially available expression vector portfolio which comprise an assortment of vectors complete with well-established methods which consistently demonstrate tissue-specific expression and inducible tissue-specific expression. The GENOVO Corporation is an example source for vectors and methods to practice gene-therapy methods of the present invention. Nucleic acid coding regions of the present invention are incorporated into effective expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, DNA derived from SEQ ID NO:1, e.g., derivatives which encode dominant negative mutants or antisense molecules contemplated herein, can be transferred into cells for gene therapy by non-viral techniques including direct microinjection, receptor-mediated targeted DNA transfer using ligand-DNA conjugates or adenovirus-ligand-DNA conjugates, or lipofection membrane fusion. These procedures and variations thereof are suitable for ex vivo, as well as in vivo human signal-transduction kinase polypeptide gene therapy according to established methods in this art.

Generally Acceptable Vectors

In accordance with the present invention, polynucleotide sequences which encode KOD, fragments of the polypeptide, dominant negative mutant versions, fusion proteins, or antisense molecules may be used in recombinant DNA molecules that direct the expression of the respective molecule in appropriate host cells. Due to the inherent degeneracy of the genetic code, other DNA sequences which encode substantially the same or a functionally equivalent amino acid sequence may be used to clone and express the mediator of apoptosis, as well as variations thereto and dominant negative mutants thereof. As will be understood by those of skill in the art, it may be advantageous to produce nucleotide sequences possessing non-naturally occurring codons.

KOD cDNA, e.g., SEQ ID NO:1, may be recombinantly expressed by molecular cloning into an expression vector containing a suitable promoter and other appropriate transcription regulatory elements, and transferred into prokaryotic or eukaryotic host cells to produce the native biomolecule. Techniques for such manipulations are fully described in Sambrook, J., et al., Molecular Cloning Second Edition, Cold Spring Harbor Press (1990), and are well known in the art.

Expression vectors are described herein as nucleic acid sequences for the transcription of embodiments of the present invention. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the KOD molecule as well as variants and derivativescontemplated herein. Commercially available mammalian expression vectors which are suitable for recombinant expression, include but are not limited to, pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically acive KOD. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual*, 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes the activator of apoptosis of the present invention may be cultured under conditions suitable for the expression and recovery of the encoded protein from cell culture. Embodiments of the present invention are host cells transformed with a purified polynucleotide comprising a nucleic acid sequence to encode the polypeptide having the sequence as depicted in SEQ ID NO:3 or a contemplated variant thereof. Cells of this type or preparations made from them may be used to screen for modulators of the biological and/or pharmacological activity of the native molecules SEQ ID NO:1, SEQ ID NO:2, and SEQ ID NO:3.

Eukaryotic recombinant host cells are especially preferred. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616),BS-C-1 (ATCC CCL 26) and MRC-5 (ATCC CCL 171).

The expression vector may be introduced into host cells to express the activator of apoptosis, KOD and derivatives thereof via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of KOD production. Identification of host cell clones which express KOD may be performed by several means, including but not limited to immunological reactivity with antibodies described herein, and/or the presence of host cell-associated specific biological activity, and/or the ability to covalently cross-link specific substrate to the novel kinase with the bifunctional cross-linking reagent disuccinimidyl suberate or similar cross-linking reagents.

The activator or mediator of apoptosis of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif. 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and the coding region is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, W138, NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express SEQ ID NO:2/SEQ ID NO:3, for example, may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

KOD can be produced in the yeast S.cerevisiae following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, the kinase cistron is ligated into yeast expression vectors which may employ any of a series of well-characterized secretion signals. The levels of expressed novel kinase are determined by the assays described herein.

A variety of protocols for detecting and measuring the expression of the novel molecule as well as functional derivatives thereof, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Methods —a Laboratory Manual*, APS Press, St Paul Minn.; Maddox, D. E., et al., J. Exp. Med. 158:1211.

Screening Assays

Methods are provided to screen compounds individually, or libraries of compounds, for the identification of compounds which have the ability to modulate a biological and/or pharmacological activity of a mediator of apoptosis, particularly the SEQ ID NO:3 KOD described herein. The present invention is also directed to methods of screening for compounds which modulate the expression (transcription and/or translation) of DNA or RNA encoding KOD, SEQ ID NO:3. Compounds which modulate these activities may be DNA, RNA, peptides, proteins, or non-proteinaceous organic molecules (e.g., small molecule drug compounds).

Compounds may modulate an ultimate biological and/or pharmacological activity by increasing or attenuating the expression of DNA or RNA encoding the activator of apoptosis or a function of the native SEQ ID NO:3. Compounds that modulate the expression of DNA or RNA encoding the human signal-transduction kinase polypeptide or the function of the polypeptide may be detected by a variety of assays. The assay may be a simple "yes/no" assay to determine whether there is a change in expression or activity. The assay may be made quantitative by comparing the expression or function of a test sample with the levels of expression or function in a standard sample.

The activator of apoptosis described herein, its functional fragments or oligopeptides can be used for screening therapeutic compounds in any of a variety of drug screening techniques. The fragment or entity employed in such a test may be free in solution, affixed to a solid support, borne on a cell surface, or located intracellularly. The abolition or modulation of activity or the formation of binding complexes, between the KOD molecule and the agent being tested, may be measured, for example, by means provided (see, Examples appended hereto). Accordingly, the present invention provides a method for screening a plurality of compounds for specific binding affinity with the native polypeptide SEQ ID NO:3 or a variant thereof contemplated herein, comprising providing a plurality of compounds; combining an embodiment of KOD of the present invention with each of a plurality of compounds for a time sufficient to allow binding under suitable conditions; and detecting binding of an embodiment of the activator of apoptosis, to each of the plurality of compounds, thereby identifying the compounds which specifically bind the KOD polypeptide.

Methods of identifying compounds that modulate a biological and/or pharmacological activity of a mediator of apoptosis are generally preferred, which comprise combining a candidate compound modulator with a polypeptide comprising the sequence as depicted in SEQ ID NO:3 or a variant thereof contemplated herein (e.g., SEQ ID NO:7, or SEQ ID NO:8, or an effective portion thereof), and measuring an effect of the candidate compound modulator on the biological and/or pharmacological activity of the polypeptide.

Methods of identifying compounds that modulate a biological and/or pharmacological activity of a protein which mediates apoptosis are particularly preferred which comprise combining a candidate compound modulator with a host-cell expressing a polypeptide having the sequence as depicted in SEQ ID NO:3 or a variant thereof contemplated herein (e.g., SEQ ID NO:7, or SEQ ID NO:8, or an effective portion thereof), and measuring an effect of the candidate compound modulator on the biological and/or pharmacological activity of the polypeptide. Preferred cellular assays for modulators of KOD fall into two general categories: 1) direct measurement of a biological activity, and 2) measurement of downstream events in the signaling cascade including cell/tissue/organism physiological manifestations. See Examples appended hereto.

A filter assay based on the protocol of Reuter et al. (1995) is also used to screen for compounds which modulate kinase activity, for example, of SEQ ID NO:3. See, Example VI.

In another embodiment of the invention to identify agents which modulate a biological activity of the novel biomolecule set forth herein, a nucleic acid sequence which encodes a human signal-transduction molecule as depicted in SEQ ID NO:3 may be ligated to a heterologous sequence to encode a fusion protein for use in a yeast 2-hybrid system. To screen compounds for the modulation of SEQ ID NO:3 biological activity, it is necessary to encode a chimeric kinase molecule as described herein for expression in hererologous host cells. Chimeric constructs are also used to express a 'bait', according to methods well known using a yeast two-hybrid system, using accessory native peptides that are expected to be associated with KOD, e.g., CRADD, RAIDD, TRADD, SODD, TNF-R1, TRAF2, FasR, DR3, DR4 and/or DR5. The two-hybrid system uses the ability of a pair of interacting proteins to bring a transcription activation domain into close proximity with a DNA-binding site that regulates the expression of an adjacent reporter gene. Compounds which are able to modulate the biological activity of the novel biomolecule as defined herein are identified by the their ability to effect protein:protein interactions (reconstitution of the chimeric transcriptional activators) and hence the yeast 2-hybrid readout assays well-known to artisans of ordinary skill in this area of molecular biology. Fields, S., et al., Trends Genet., 10:286 (1994); Allen, J. B., et al., TIBS, 20:511 (1995). Fields, S., Song, O., Nature 340:245 (1989). Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Sternglanz, R., TIG, 10(8):286 (1994); and U.S. Pat. No. 5,283,173, System to Detect Protein-Protein Interactions, and U.S. Pat. No. 5,468,614, which are incorporated herein by reference.

To further evaluate the ability of a compound to modulate the pharmacological activity, for example, of SEQ ID NO:3, human tumor cells are injected into SCID mice (severe combined immunodeficiency) to form palpable tumor masses. See, Example V.

Compounds which are identified generally according to methods described, contemplated, and referenced herein that modulate a biological and/or pharmacological activity of a protein which mediates apoptosis, e.g., the sequence as depicted in SEQ ID NO:3, are especially preferred embodiments of the present invention.

An especially preferred embodiment of the present invention is a method for treatment of a patient in need of such treatment for a dysfunctional-apoptosis related condition which is mediated by a human activator of apoptosis, e.g., SEQ ID NO:3, comprising administration of a therapeutically effective amount of a modulating compound identified using sequences comprising sequences as depicted in SEQ ID NO:1 and/or SEQ ID NO:3 or a contemplated variant thereof as a pharmacological target in methods contemplated herein.

A method of modulating a biological and/or pharmacological activity of a protein which mediates apoptosis in a cell, tissue, or organism is preferred which comprises administering an effective amount of a polynucleotide comprising a nucleic acid sequence derived from SEQ ID NO:1 contemplated herein including but not limited to nucleic acid sequences which encode biologically effective fragments, dominant negative mutant versions, and antisense molecules.

Antibodies

Specific antibodies to the KOD polypeptide of the present invention are purified from mammalian antisera containing antibodies reactive against the polypeptide or are prepared as monoclonal antibodies reactive with the signal transduction polypeptide using the technique of Kohler and Milstein, Nature, 256:495 (1975). Mono-specific antibody as used herein is defined as a single antibody species or multiple antibody species with homogenous binding characteristics for the novel signal transduction molecule. Homogenous binding as used herein refers to the ability of the antibody species to bind to a specific antigen or epitope, such as those associated with the signal transduction kinase, as described. KOD specific antibodies are raised by immunizing animals such as mice, rats, guinea pigs, rabbits, goats, horses and the like, with rabbits being preferred, with an appropriate concentration of the human signal transduction kinase either with or without an immune adjuvant. Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art. In vitro production of the anti-KOD polypeptide mAb is carried out by growing the hydridoma in DMEM containing about 2% fetal calf serum to obtain sufficient quantities of the specific mAb. The mAb are purified by techniques known in the art.

Purification of SEQ ID NO:3 via Affinity Columns

It is readily apparent to those skilled in the art that methods for producing antibodies may be utilized to produce antibodies specific for KOD polypeptide fragments, or the full-length nascent polypeptide, e.g., SEQ ID NO:3. Specifically, it is readily apparent to those skilled in the art that antibodies may be generated which are specific for the fully functional protein or fragments thereof.

KOD antibody affinity columns are made by adding the antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing KOD using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. Purified KOD polypeptide is then dialyzed against phosphate buffered saline/detergent.

Recombinant KOD molecules can be separated from other cellular proteins by use of an immunoaffinity column made with monoclonal or polyclonal antibodies specific for full length nascent KOD, or polypeptide fragments of the apoptosis activator molecule.

KOD polypeptides described herein may be used to affinity purify biological effectors from native biological materials, e.g. disease tissue. Affinity chromatography techniques are well known to those skilled in the art. A KOD peptide described herein or an effective fragment thereof, is fixed to a solid matrix, e.g. CNBr activated Sepharose according to the protocol of the supplier (e.g., Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

Diagnostic Assays

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar diagnostic assays are used to detect the presence of the KOD polypeptide in body fluids or tissue and cell extracts.

Diagnostic assays using KOD-specific antibodies are useful for the diagnosis of conditions, disorders or diseases characterized by abnormal expression of the activator of apoptosis or expression of genes associated with apoptosis. Diagnostic assays for KOD include methods utilizing the antibody and a label to detect SEQ ID NO:3 in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule, a myriad of which are well-known to those skilled in the art.

A variety of protocols for measuring the KOD polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the human signal-transduction kinase polypeptide is preferred, but a competitive binding assay may be employed. These assays are described, among other places, in Maddox, D. E. et al., *J. Exp. Med.* 158:1211 (1983); Sites, D. P., et al., *Basic and Clinical Immunology*, Ch.22, 4th Ed., Lange Medical Publications, Los Altos, Calif. (1982); U.S. Pat. Nos. 3,654,090, 3,850,752; and 4,016,043.

In order to provide a basis for the diagnosis of disease, normal or standard values for KOD normal expression levels must be established. This is accomplished by combining body fluids or cell extracts taken from normal subjects, either animal or human, with antibody to KOD under conditions suitable for complex formation which are well known in the art. The amount of standard complex formation may be quantified by comparing it with a dilution series of positive controls where a known amount of antibody is combined with known concentrations of purified human signal-transduction kinase polypeptide. Then, standard values obtained from normal samples may be compared with values obtained from samples from subjects potentially affected by a disorder or disease related to expression of the activator of apoptosis. Deviation between standard and subject values establishes the presence of the disease state (e.g., Alzheimer's disease).

Kits containing a nucleic acid derived from SEQ ID NO:1, antibodies to a corresponding polypeptide, or protein, e.g., SEQ ID NO:3 may be prepared. Such kits are used to detect heterologous nucleic acids which hybridize to a nucleic acid pertaining to the KOD described herein, or to detect the presence of protein or peptide fragments in a sample. Such characterization is useful for a variety of purposes including, but not limited to, diagnosis of a dysfunctional-apoptosis condition, as well as forensic analyses, and epidemiological studies.

The DNA molecules, RNA molecules, recombinant protein and antibodies of the present invention may be used to screen and measure levels of KOD DNA, RNA or protein. A kit comprises a compartmentalized carrier suitable to hold in close confinement at least one container. The carrier would further comprise reagents such as PCR primers derived from SEQ ID NO:1 or anti-kinase antibodies suitable for detecting the novel molecule as depicted in SEQ ID NO:3. The carrier may also contain a means for detection such as labeled antigen or enzyme substrates or the like.

Polynucleotide sequences which encode the activator of apoptosis may be used for the diagnosis of dysfunctional-apoptotic conditions. For example, polynucleotide sequences which encode KOD may be used in hybridization or PCR assays of fluids or tissues from biopsies to detect expression of the activator. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regime in animal studies, in clinical trials, or in monitoring the treatment of an individual patient. Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR Diagnostics

SEQ ID NO:1, oligonucleotides, fragments, portions or antisense molecules thereof, may be used in diagnostic assays of body fluids or biopsied tissues to detect the expression level of the novel human signal-transduction kinase molecule. For example, sequences designed from the cDNA sequence SEQ ID NO:1 or sequences comprised in SEQ ID NO:2 can be used to detect the presence of the mRNA transcripts in a patient or to monitor the modulation of transcripts during treatment.

One method for amplification of target nucleic acids, or for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. One example embodiment of the present invention is a diagnostic composition for the identification of a polynucleotide sequence comprising the sequence as depicted in SEQ ID NO:2 comprising PCR primers derived from SEQ ID NO:1. See, Example I (SEQ ID NO:10 and SEQ ID NO:11). The degree of amplification of a target sequence is controlled by the number of cycles that are performed and is theoretically calculated by the simple formula 2n where n is the number of cycles. See, e.g., Perkin Elmer, *PCR Bibliography*, Roche Molecular Systems, Branchburg, N.J.; CLONTECH products, Palo Alto, Calif.; U.S. Pat. No. 5,629,158, Solid Phase Diagnosis of Medical Conditions, issued May 13, 1997.

Compositions

Pharmaceutically useful therapeutic compositions which comprise a derivative nucleic acid of SEQ ID NO:1, a dominant negative mutant coding region, an antisense sequence, a polypeptide as depicted in SEQ ID NO:3 or a variation thereof contemplated herein, or a compound identified by means encompassed by the claims appended hereto that modulates the biological and/or pharmacological activity a protein which mediated apoptosis, e.g., SEQ ID NO:3, may be formulated according to known methods such as by the admixture of a pharmaceutically acceptable carrier. Examples of such carriers and methods of formulation may be found in *Remington's Pharmaceutical Sciences* (Maack Publishing Co, Easton, PA.). To form a pharmaceutically acceptable composition suitable for effective administration, such compositions will contain an effective amount of a polypeptide, nucleic acid, or compound modulator.

Therapeutic or diagnostic compositions of the invention are administered to an individual or used in amounts sufficient to treat or diagnose apoptosis-related disorders. The effective amount may vary according to a variety of factors such as the individual's condition, weight, sex and age. Other factors include the mode of administration.

The term functional derivative includes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of compound, peptide, or nucleic acid which ameliorate or prevent a dysfunctional apoptotic condition. The exact dosage is chosen by the individual physician in view of the patient to be treated.

Compounds identified according to the methods disclosed herein as well as therapeutic nucleic acids and peptides contemplated herein may be used alone at appropriate dosages defined by routine testing in order to obtain optimal modulation of KOD activity. In addition, co-administration or sequential administration of these and other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of a protein which mediates apoptosis can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound, nucleic acid, or peptide desired can be employed as an apoptosis modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of KOD modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

Full Length Clone

A pair of primers were designed to contain 5' plus-strand sequence starting with the ATG (start codon) and 3' minus-strand sequence starting at the TAG (the stop codon) NotI restriction sites at both ends. The 5' primer is: SEQ ID NO:10. The 3' primer is: SEQ ID NO:11. The full length coding region of KOD was then amplified by PCR with these primers and high-fidelity Vent DNA polymerase (New England Biolabs, Inc, #254) using plasmid DNA as template. The product was cut with NotI, phenol-precipitated and ligated into pIRES-EGFP (Clontech #6064-1). This recombinant DNA was amplified in $E.coli$ and the DNA sequence was confirmed by sequencing. DNA sequencing was performed using an Applied Biosystems Model 377 Automated DNA Sequencer and standard fluorescent dye terminator chemistry.

Example II

Assay for Kinase Activity

Recombinant, purified GST/SEQ ID NO:3 (or other peptide derived from SEQ ID NO:3, e.g., a polynucleotide comprising SEQ ID NO:6) is added to 20 μg myelin basic protein (MBP) in 10 μL of a 3× kinase reaction buffer (KRB) containing (in mM): 60 HEPES (pH 7.5), 30 magnesium acetate, 0.15 ATP, 3 DTT, 0.03 sodium orthovanadate. The reaction is started by the addition of 5 μCi [γ-$^{32}$P]ATP (10 μL). Samples are incubated for 5 minutes at 30° C. The reaction stopped by addition of 4× Laemmli sample buffer. Proteins are separated on 12% Tris/glycine SDS gels, stained with Coomassie blue, dried and exposed to autoradiograph film.

Example III

Cell Culture and Transfection Assays

HeLa (American Type Culture Collection, Accession Number CCL-2) were grown in DMEM supplemented with 10% fetal calf serum, 100 U/ml penicillin and 0.1 mg/ml streptomycin. A 549 cells, a human lung carcinoma cell line (American Type Culture Collection, Accession Number CCL-185) were grown in F-12K medium supplemented with 10% fetal calf serum, 100 U/ml penicillin and 0.1 mg/ml streptomycin. Cells were transfected by electroporation using 5–10 micrograms of pIRES/KOD (SEQ ID NO:1) plasmid DNA in 250 microliters DMEM plus fetal calf serum and a Bio-Rad Gene Pulser II at the settings 0.22 Kr, 0.96 μF, 40–50 microseconds. FADD is used as a positive control in this case and is known to induce apoptosis. Chinnaiyan, A.M., et al., Cell, 81(4):505 (1995). When BCL-xL (a suppressor of apoptosis) is co-transfected with KOD into HeLa cells, the cells are rescued from death. See, Boise, L. H., et al., Cell, 74(4):597 (1993). KOD induced apoptosis is also blocked by ZVAD (an inhibitor of caspase-dependent apoptosis). See, Garcia-Calvo, M., et al., J. Biol. Chem., 273(49):32608 (1998).

He La cells were split 24 hours prior to transfection. 2×10$^6$ cells were transfected with pIRES vector as negative control.

After the cells were electroporated (10 microgram DNA, 2×10$^6$ cells in 250 microliters of DMEM with 10% FBS and 100 U/ml penicillin, 100 microgram/ml streptomycin; 0.22 kV, 950 microFarads, 0.4 cm cuvette) with equal amounts of DNA, they were seeded into a six-well plate with a cover slip in each well. At least 24 or 48 hours, the cover slips were picked and cells on them were fixed with 4% paraformaldehyde. With or without staining with the DNA stain, DAPI (4,6-diamidino-2-phenylindole) the coverslips were mounted on slides and examined by fluorescence microscopy. The percentage of green (fluorescent) cells from experimental samples were normalized according to the pIRES negative control. The cell survival rates were the summary of three independent experiments.

When KOD was overexpressed in He La cells, 80–95% of cells containing the protein died by apoptosis. Apoptosis was verified by cell morphology. By contrast, there was nearly 100% survival of cells transfected with the pIRES vector only. See, FIG. 1.

Example IV
Northern Blot Analysis

A 989 bp PCR product corresponding to 450 bp of 3'coding sequence and 539 bp of 3'untranslated region of KOD SEQ ID NO:1 was used to make a probe for northern blots. The PCR product was labeled using a random, hexanucleotide priming kit (Boehringer Mannheim cat # 1004760) and alpha-$P^{32}$-dCTP (Amersham, 3000 Ci/millimole). The procedure was carried out according to the manufacturer's protocol. Multiple tissue blots and tumor cell line blots were purchased from Clonetech, and using the manufacturer's protocol. After drying the blot membranes were exposed to Kodak XAR5 film with an intensifying screen at −80° C. For 72 hours. Alternatively the blot membranes were quantified by use of a phosphorimager (Molecular Dynamics, Storm) with an exposure of 1 hour. This gave a relative intensity for each tissue or cell line.

Example V
Efficacy (pharmacological activity) Screen

To further evaluate the ability of a compound, polynucleotide, or peptide to inhibit human tumor growth, for example, human tumor cells are injected into SCID mice (severe combined immunodeficiency) to form palpable tumor masses. The effects of various doses (e.g., 1–50 mg) of a compound in inhibiting tumor growth can be determined as follows: approximately $1 \times 10^7$ cells of the CCL 221 cell line (ATCC, Rockville, Md.), a human ras-dependent colon adenocarcinoma cell line, is suspended in 100 $\mu l$ DMEM and injected subcutaneously into SCID mice, such that two tumors per mouse are formed. SCID mice receive CCL 221 cells and the tumors are grown for 7 days without treatment; on the 7th day (Day 0) tumor maximal diameters and animal weights are recorded and the mean tumor size for the mice is determined. On Day 1 (eight days following tumor cell injection), treatment of the mice with the candidate compound or vehicle alone is begun. One group of the mice (controls) are injected intraperitoneally with 0.2 ml of vehicle and a second group of mice receives compound by intraperitoneal injection. Various doses (0.25–75 mg) of the compound can be tested in separate groups of mice. On Day 7 and Day 14, animal weight and maximal tumor diameter is measured. Average maximal tumor size for each group on Day 0, Day 7, and Day 14 are compared Day 14, one high dose animal is followed for an additional to determine whether the agent produces a dose-dependent inhibition of tumor growth. Toxicity effects can be examined by tracking mice weight and by harvesting lungs, livers, and spleens of the animals for histological staining.

Example VI
High Throughput Screening for Compounds which Modulate Activity

High throughput screening for modulator compounds is performed using MBP coated 96-well FlashPlates® (NEN™ Life Science Products). Kinase reaction buffer (3× kinase reaction buffer (KRB) contains: 60 mM HEPES (pH 7.5), 30 mM magnesium acetate, 0.15 mM ATP, 3 mM DTT, 0.03 mM sodium orthovanadate) 0.25 $\mu$Ci [$\gamma^{33}$P]-ATP at a concentration no greater than 1 $\mu$g/ml, (determined by titration of individual enzyme preparations for a concentration that allows kinetic determinations over a 1 hour time course of the human KOD, or other peptide derived from SEQ ID NO:3, e.g., a polynucleotide comprising SEQ ID NO:6, are added to each well and incubated 1 hour at 30° C. in the presence or absence of 10 $\mu$M test compound. Total reaction volume is 100 $\mu$L. Following incubation, the reaction mixture is aspirated and the wells rinsed 2 times with 300 $\mu$L PBS. Incorporation of raiolabeled phosphate is determined by scintillation counting, Packard Instrument Co.TopCount, 12-detector, 96-well microplate scintillation counter and luminescence counter, model B991200. Compounds which inhibit kinase activity $\geq$50 percent at 10 $\mu$M are indicated by a >50% reduction in scintillation counts. Specificity and selectivity are determined by titration of inhibitory compounds to determine the $IC_{50}$ (or other standard quantitation well known in the art for comparison) and by the substitution of other kinases in the assay. For example, determination of relative inhibitory activity of the kinase in comparison to recombinant RIP and/or DAP, expressed and isolated in a similar manner, assayed under similar conditions, provides selectivity data.

Alternatively, a filter assay based on the protocol of Reuter et al. (1995) may be used. This protocol is the same but the reaction is stopped by the addition of EDTA (pH 7.0) to a final concentration of 80 mM. Samples are then centrifuged and 50 $\mu$L of the supernatant spotted on p81 cation-exchange filter paper (Whatman, No. 3698 915). The filters are then washed 3 times in 200 mL of 180 mM $H_3PO_4$ (5–10 min each) and once in 200 mL of 96% ethanol. After air drying the filters, radioactivity is determined by Cerenkov counting in a scintillation counter. Reuter, C. W. M., Catling, A. D. and Weber, M. J., Immune Complex Kinase Assays for Mitogen-Activated Protein Kinase and MEK, Methods In Enzymology, 255:245 (1995).

Example VII
High Throughput Screening Protocol

Test compounds Test compounds are prepared in advance from 2.5 mg/ml stock solutions in DMSO by diluting 1:10 in distilled water and then 1:10 again. Ten (10)$\mu l$ of the 1:100 dilution solutions (25 $\mu$g/ml in 1% DMSO) are prepared in 96 well Microlite 1 plates (Dynatech) and plates are stored at −20° C. until the evening prior to the start of the assay.

Control Plates

A plate containing control solutions is included in each run of the screen for QA purposes. Such plates are prepared at the beginning of the HTS campaign and stored at −20° C. until required. Zero inhibition (MAX. signal) wells (columns 3, 6, 8 and 10) contain 10 $\mu l$ of 1% (v/v) DMSO solution in MilliQ water. 100% inhibition (MIN signal) wells (columns 1, 4, 9 and 11) contain 10 $\mu l$ of 220 nM ZM333141/1 in 1% DMSO solution in MilliQ water. 50% inhibition (REF. signal) wells (columns 2, 5, 7 and 12) contain a reference compound at a concentration known to provide approximately 50% inhibition in 1% (v/v) DMSO solution in MilliQ water.

Assay Components (1) recombinant KOD or other peptide derived from SEQ ID NO:3, e.g., a polynucleotide comprising SEQ ID NO:6 (expressed in *E.coli* or eukaryotic cells as described herein) or a lysate of a prokaryotic or eukaryotic cell expressing recombinant enzyme, or the natural enzyme partially purified from a human cell line.

(2) [γ-$^{33}$-P]-adenosine triphosphate (3) myelin basic protein linked to the surface of PVT SPA beads (purchased from Amersham International) by an antibody-protein A or other appropriate method.

To Microlite I plates containing 10 μl of test compound, which have been left on the bench overnight to reach room temperature, 25 ml of GST-Rb/ATP/ATP$^{33}$ is added, immediately followed by 20 μl of Enzyme, using two Multidrops. The plates are stacked in 13 plate stacks (with an empty plate on top of each stack to minimise evaporation firom the top plate) and left at room temperature for 105 minutes. 150 μl of "Stop Solution" containing beads antibody and EDTA is added using a Multidrop. The plates are sealed with Topseal-S plate scalers and left on the bench overnight, surrounded by Scotlab perspex screens. The plates arc then centrifuged (Heraeus Megafuge 3.0R) at 2500 rpm, 1124×g., for 5 minutes (2 plates per trunnion) and counted on a Topcount (14.34); (isotope:P$^{33}$; counting time: 20 seconds/well).

The data may be analysed using well-known software systems. A threshold for inhibition is set, e.g., 60% inhibition of scintillation signal. Compounds reaching the inhibition threshold are scored as active.

Example VIII
In Vitro Autophosphorylation Assay

Coding sequences of the KOD wild-type (SEQ ID NO:3) and dominant negative mutant, K50R (SEQ ID NO:4), for example, were PCR cloned into the KpnI-NotI sites in the pMH vector (Cat# 1814702, Boehringer Mannheim, Indianapolis, Ind.) to encode a C-terminal HA epitope tag. KOD-HA and K50A-KOD-HA were prepared by in vitro translation from these vectors using the TNT T7 reticulocyte lysate system (Cat# L4610, Promega Corp., Madison, Wis.) according to the manufacturer's specifications. The proteins were immunoprecipitated using a rat monoclonal antibody against HA (Cat# 1867423, Boehringer Mannheim, Indianapolis, Ind.) in NETN buffer [20 mM Tris (pH 8.0), 100 mM NaCl, 1 mM EDTA, and 0.2% NP-40] for 2 hours at 4° C. followed by protein A-sepharose (Cat# 17078001, Pharmacia Biotech, Piscataway, N.J.). The samples were washed twice in NETN buffer and then incubated in 100 μl of kinase buffer [40 mM HEPES (pH 7.4), 5 mM MgCl$_2$, 150 μM CaCl$_2$, 100 μM EGTA, 50 μM dATP] supplement with 10 μCi $^{32}$γP-dATP (Cat# NEG200A, NEN, Boston, Mass.) at 30° C. for 30 min. The samples were washed twice in kinase buffer, resuspended in 2× Laemmli buffer, boiled for 5 min, and then resolved by SDS-PAGE. Gels were fixed in 50% methanol, 10% acetic acid for 1 hr, dried and then visualized by autoradiography.

Example IX
General PCR Method for Generation of Fragments for Generation of KOD Mutants The PCR method used for all the mutants of KOD was the same. The plasmid that contained the full length coding region of KOD was used as template in a PCR with the specific primers (described in Examples which follow) and high-fidelity Vent DNA polymerase (New England Biolabs, Inc, #254) for 30–35 cycles. For each each construct in which there are point mutations, two overlapping fragments were made such that in the mutation occurred in the middle of the overlapping region. Then the two, gel purified, overlapping fragments were used in a second round of PCR (same conditions) to create a full length KOD construct with the mutation. For domain deletion mutants, PCR was used to sub-clone the appropriate, remaining DNA. All final recombinant DNA constructs were cut with appropriate restriction enzymes, ligated into the pTracer vector, amplified in E.coli and the DNA sequence was confirmed by sequencing. DNA sequencing was performed using an Applied Biosystems Model 377 Automated DNA Sequencer and standard fluorescent dye terminator chemistry.

Example X
Construction of Dominant Negative Mutant SEQ ID NO:4

SEQ ID NO:4 encodes, D143A, a SEQ ID NO:3 kinase domain mutant in the kinase active site. PCR primers SEQ ID NO:12 and SEQ ID NO:13 are used to generate a PCR fragment (F1). SEQ ID NO:14 and SEQ ID NO:15 PCR primers are used to generate a PCR fragment (F2). Gel-purify the two fragments. PCR primers SEQ ID NO:16 and SEQ ID NO:17 are used along with the newly generated PCR fragments (F1+F2) to synthesize the full length of KOD cDNA corresponding to SEQ ID NO:3 position 143 amino acid change (D to A) (SEQ ID NO:4) by PCR amplification. This fragment is cut with SmaI and NotI and ligated into pTracer.

Example XI
Construction of Dominant Negative Mutant SEQ ID NO:5

SEQ ID NO:5 encodes, K50R, a SEQ ID NO:3 kinase domain mutant in the ATP binding site. Primers SEQ ID NO:18 and SEQ ID NO:19 are used to generate a PCR fragment (F1). Primers SEQ ID NO:20 and SEQ ID NO:21 are used to generate a second PCR fragment (F2). Gel-purify the two fragments. PCR primers SEQ ID NO:22 and SEQ ID NO:23 and the newly generated PCR fragments (F1+F2) are used to synthesize the full length of KOD cDNA with change (K50 to R) by PCR amplification. This fragment is cut with SmaI and NotI and ligated into pTracer.

Example XII
Construction of Death Domain, SEQ ID NO:7

SEQ ID NO:7 encodes the KOD death domain of SEQ ID NO:3. Primers SEQ ID NO:24 and SEQ ID NO:25 are used to generate a PCR fragment. The gel purified fragment is cut with NotI and EcoRI and ligated into pTracer.

Example XIII
Construction of SEQ ID NO:8

SEQ ID NO:8 encodes the delta (removed) death domain mutant of SEQ ID NO:3. Primers SEQ ID NO:26 and SEQ ID NO:27 are used to generate a PCR fragment. The gel purified fragment is cut with SmaI and NotI and ligated into pTracer

Example XIV
Construction of Dominant Negative Mutant SEQ ID NO:9

SEQ ID NO:9 encodes the dominant negative mutant of SEQ ID NO:3 wherein tryptophans at positions 435 and 478 are changed to alanine. The changes in this mutant were generated sequentially. To generate a coding region corresponding to an amino acid change of W to A in position 435, PCR primers SEQ ID NO:28 and SEQ ID NO:29 are used to generate a fragment (F1). PCR primers SEQ ID NO:30 and SEQ ID NO:31 are used to generate another fragment (F2). Gel-purify the two fragments. PCR primers SEQ ID NO:32 and SEQ ID NO:33 and the newly generated PCR fragments (F1+F2) are used to synthesize (by PCR amplification) the full length dominant negative cDNA corresponding to the first amino acid change. The product fragment is cut with SmaI and NotI and ligated into pTracer which is used as the template for the second step: PCR primers SEQ ID NO:34 and SEQ ID NO:35 are used to generate a PCR product fragment (F3). PCR primers 36 and 37 are used to generate another fragment (F4). Gel-purify the two fragments. PCR primers 38 and 39 and the newly generated PCR fragments are used (F3+F4) to synthesize the full length mutant cDNA by PCR amplification. The gel purified fragment is cut with SmaI and NotI and ligated into pTracer.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising the amino acid sequence as depicted in SEQ ID NO:3 or a variant of SEQ ID NO:3 having at least about 80% homology to a member selected from the group consisting of: SEQ ID NO:3, SEQ ID NO:6, SEQ ID NO:7, and SEQ ID NO:8, wherein said variant has biological or pharmacological activity of an amino acid sequence as depicted in SEQ ID NO:3, or is capable of modulating the biological or pharmacological activity of an amino acid sequence as depicted in SEQ ID NO:3.

2. A method of identifying compounds that modulate a biological and/or pharmacological activity of a protein which mediates apoptosis, comprising:
 (a) combining a candidate compound modulator with a polypeptide comprising the amino acid sequence as depicted in SEQ ID NO:3 or a variant of SEQ ID NO:3 having at least about 80% homology to a member selected from the group consisting of: SEQ ID NO:3, SEQ ID NO:6, SEQ ID NO:7, and SEQ ID NO:8, wherein said variant has biological or pharmacological activity of an amino acid sequence as depicted in SEQ ID NO:3,
 (b) measuring an effect of said candidate compound modulator on said biological and/or pharmacological activity of said polypeptide, and
 (c) selecting those compounds which alter the biological and/or pharmacological activity of said amino acid sequence as those that modulate a biological and/or pharmacological activity of a protein which mediates apoptosis.

3. The method of claim 2 of identifying compounds that modulate a biological and/or pharmacological activity of a protein which mediates apoptosis comprising:
 (a) combining said candidate compound modulator with said polypeptide expressed in a host-cell,
 (b) measuring the effect of the candidate compound modulator on the biological and/or pharmacological activity of the polypeptide, and
 (c) selecting those compounds which alter the biological and/or pharmacological activity of the polypeptide as those that modulate a biological and/or pharmacological activity of a protein which mediates apoptosis.

4. A polypeptide according to claim 1 wherein one or more amino acids of SEQ ID NO:3 selected from aspartic acid 143; lysine 50; tryptophan 435 and tryptophan 478 are replaced or deleted.

5. A polypeptide according to claim 1 which is a biologically effective dominant negative mutant variant of SEQ ID NO:3 having an ability to modulate the biological and/or pharmacological activity of an apoptosis activator having a sequence as depicted in SEQ ID NO:3.

* * * * *

Adverse Decision in Interference

Patent No. 6,267,956, Bruce Charles Gomes, Garrett M. Kasof, Judith Caroline Prosser, PROTEIN ACTIVATOR AND APOPTOSIS, Interference No. 105,360, final judgment adverse to the patentees rendered April 4, 2006, as to claims 1-5.

*(Official Gazette February 13, 2007)*